United States Patent
Levy et al.

(10) Patent No.: US 7,468,384 B2
(45) Date of Patent: Dec. 23, 2008

(54) MICROBICIDAL COMPOSITION

(75) Inventors: Richard Levy, Valbonne (FR); Megan Anne Diehl, Line Lexington, PA (US); Dolores Ann Shaw, Collegeville, PA (US); Eileen Fleck Warwick, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 253 days.

(21) Appl. No.: 11/265,654

(22) Filed: Nov. 2, 2005

(65) Prior Publication Data
US 2006/0106024 A1 May 18, 2006

Related U.S. Application Data

(60) Provisional application No. 60/628,326, filed on Nov. 16, 2004.

(51) Int. Cl.
*A01N 43/80* (2006.01)
*A61K 31/425* (2006.01)

(52) U.S. Cl. .................................... 514/373
(58) Field of Classification Search ............ None
See application file for complete search history.

(56) References Cited

U.S. PATENT DOCUMENTS

| | | | |
|---|---|---|---|
| 4,173,643 A | 11/1979 | Law | |
| 4,295,887 A | 10/1981 | Buckley et al. | |
| 4,352,744 A | 10/1982 | Bettinger et al. | |
| 4,454,146 A | 6/1984 | Borovian et al. | |
| 4,725,612 A | 2/1988 | Mahn et al. | |
| 4,906,651 A | 3/1990 | Hsu | |
| 4,964,892 A | 10/1990 | Hsu | |
| 5,008,150 A | 4/1991 | Ashida et al. | |
| 5,125,967 A | 6/1992 | Morpeth et al. | |
| 5,160,666 A | 11/1992 | Lindner et al. | |
| 5,294,614 A | 3/1994 | Hsu et al. | |
| 5,424,324 A * | 6/1995 | Willingham | 514/372 |
| 5,464,850 A | 11/1995 | Voo et al. | |
| 5,609,432 A | 3/1997 | Yamamoto et al. | |
| 5,668,083 A | 9/1997 | Matsumoto et al. | |
| 5,863,882 A | 1/1999 | Lin et al. | |
| 6,114,366 A | 9/2000 | Lutz et al. | |
| 6,133,300 A | 10/2000 | Smith et al. | |
| 6,159,999 A | 12/2000 | Yagi et al. | |
| 6,306,413 B1 | 10/2001 | Payne | |
| 6,429,220 B1 | 8/2002 | Yagi et al. | |
| 6,432,433 B1 | 8/2002 | Winkowski et al. | |
| 6,511,673 B1 | 1/2003 | Chia et al. | |
| 6,696,237 B1 | 2/2004 | Yoshioka et al. | |
| 7,045,542 B1 | 5/2006 | Beilfuss et al. | |
| 2002/0028754 A1 | 3/2002 | Johansen et al. | |
| 2004/0014799 A1 | 1/2004 | Antoni-Zimmermann et al. | |
| 2004/0198785 A1 | 10/2004 | Heer et al. | |
| 2005/0228032 A1 | 10/2005 | Merianos et al. | |
| 2006/0106131 A1 | 5/2006 | Edmunds | |

FOREIGN PATENT DOCUMENTS

| | | |
|---|---|---|
| EP | 0236119 | 9/1987 |
| EP | 0435439 | 7/1991 |
| EP | 0 787 430 | 12/1996 |
| EP | 1084619 | 3/2001 |
| EP | 1 206 933 | 11/2001 |
| EP | 1184507 | 3/2002 |
| EP | 1245153 | 10/2002 |
| EP | 1332675 | 8/2003 |
| EP | 1462003 | 9/2004 |
| EP | 1206933 B1 | 5/2006 |
| GB | 2230190 | 10/1990 |
| JP | 57156405 | 9/1982 |
| JP | 60110793 | 6/1985 |
| JP | 6313269 | 11/1994 |
| JP | 11071211 | 9/2004 |
| WO | WO 9946350 | 9/1999 |
| WO | WO 0100022 | 1/2001 |
| WO | WO 03013491 | 2/2003 |

OTHER PUBLICATIONS

Izzat, et al., "Effect of Varying Concentrations of EDTA on the Antimicrobial Properties of Cutting Fluid . . . ", Dep. Biol., Univ. of Houston, vol. 26(103), pp. 37-44 (1979).
Collier, et al., "Growth Inhibitory and Biocidal Activity of Some Isothiazolone Biocides", Journal of Applied Bacteriology, vol. 69, No. 4, pp. 569-577 (1990).

* cited by examiner

*Primary Examiner*—Sreeni Padmanabhan
*Assistant Examiner*—Samira Jean-Louis
(74) *Attorney, Agent, or Firm*—Kenneth Crimaldi

(57) ABSTRACT

A microbicidal composition of 1,2-benzisothiazolin-3-one; and at least one of benzalkonium chloride, benzethonium chloride, benzyl alcohol, caprylyl glycol, chlorphenesin, diazolidinyl urea, ethylparaben, imidazolidinyl urea, methylparaben, phenoxyethanol, linoleamidopropyl PG-dimonium chloride phosphate, cocamidopropyl PG-dimonium chloride phosphate, propylparaben, cis-1-(3-chloroallyl)-3,5,7-triaza-1-azoniaadamantane chloride, dehydroacetic acid or its salts, benzoic acid or its salts, and sodium hydroxymethylglycinate.

2 Claims, No Drawings

MICROBICIDAL COMPOSITION

CROSS REFERENCE TO RELATED PATENT APPLICATIONS

This is a non-provisional application of prior U.S. provisional Application Ser. No. 60/628,326 filed on Nov. 16, 2004.

BACKGROUND

This invention relates to a synergistic combination of selected microbicides having greater activity than would be observed for the individual microbicides.

In some cases, commercial microbicides cannot provide effective control of microorganisms, even at high use concentrations, due to weak activity against certain types of microorganisms, e.g., those resistant to some microbicides, or due to aggressive environmental conditions. Combinations of different microbicides are sometimes used to provide overall control of microorganisms in a particular end use environment. For example, combinations of 2-methyl-4-isothiazolin-3-one and other biocides are disclosed in U.S. Pat. App. Pub. No. 2004/0014799. However, there is a need for additional combinations of microbicides having enhanced activity against various strains of microorganisms to provide effective control of the microorganisms. Moreover, there is a need for combinations containing lower levels of individual microbicides for environmental and economic benefit. The problem addressed by this invention is to provide such additional combinations of microbicides.

STATEMENT OF THE INVENTION

The present invention is directed to a microbicidal composition comprising: (a) 1,2-benzisothiazolin-3-one; and (b) at least one microbicide selected from among benzalkonium chloride, benzethonium chloride, benzyl alcohol, caprylyl glycol, chlorphenesin, 2,2'-dithiobis(N-methylbenzamide), diazolidinyl urea, ethylenediamine tetraacetic acid, ethylparaben, imidazolidinyl urea, methylparaben, phenoxyethanol, linoleamidopropyl PG-dimonium chloride phosphate, cocamidopropyl PG-dimonium chloride phosphate, propylparaben, cis-1-(3-chloroallyl)-3,5,7-triaza-1-azoniaadamantane chloride, dehydroacetic acid or its salts, benzoic acid or its salts, sodium hydroxymethylglycinate and zinc pyrithione.

The present invention is further directed to a microbicidal composition comprising: (a) 2-methyl-4-isothiazolin-3-one; and (b) at least one microbicide selected from among caprylyl glycol, chlorphenesin, hexamidine diisethionate, hexetidine, linoleamidopropyl PG-dimonium chloride phosphate, cocamidopropyl PG-dimonium chloride phosphate and dehydroacetic acid or its salts.

DETAILED DESCRIPTION OF THE INVENTION

"MI" is 2-methyl-4-isothiazolin-3-one, also referred to by the name 2-methyl-3-isothiazolone. "BIT" is 1,2-benzisothiazolin-3-one. "DU" is diazolidinyl urea. "IU" is imidazolidinyl urea. "EDTA" is ethylenediamine tetraacetic acid.

As used herein, the following terms have the designated definitions, unless the context clearly indicates otherwise. The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages (%) are by weight. Amounts of organic microbicides are given on an active ingredient basis in ppm (w/w).

The compositions of the present invention unexpectedly have been found to provide enhanced microbicidal efficacy at a combined active ingredient level lower than that of the individual microbicides. In one embodiment of the invention, those antimicrobial compositions which contain halogenated 3-isothiazolones contain relatively low levels thereof, preferably no more than 1000 ppm, more preferably no more than 500 ppm, more preferably no more than 100 ppm, and most preferably no more than 50 ppm. Concentrations of halogenated 3-isothiazolones in the composition of this invention are based on the total weight of active ingredients in the composition, i.e., the microbicides exclusive of any amounts of solvents, carriers, dispersants, stabilizers or other materials which may be present. In one embodiment of the invention, the antimicrobial composition contains less than 1000 ppm of 5-chloro-2-methyl-4-isothiazolin-3-one, more preferably no more than 500 ppm, more preferably no more than 100 ppm, and most preferably no more than 50 ppm.

In one embodiment of the invention, the antimicrobial composition comprises 1,2-benzisothiazolin-3-one and benzalkonium chloride. Preferably, a weight ratio of 1,2-benzisothiazolin-3-one to benzalkonium chloride is from 1:0.025 to 1:40.

In one embodiment of the invention, the antimicrobial composition comprises 1,2-benzisothiazolin-3-one and benzethonium chloride. Preferably, a weight ratio of 1,2-benzisothiazolin-3-one to benzethonium chloride is from 1:0.13 to 1:3.

In one embodiment of the invention, the antimicrobial composition comprises 1,2-benzisothiazolin-3-one and benzyl alcohol. Preferably, a weight ratio of 1,2-benzisothiazolin-3-one to benzyl alcohol is from 1:0.4 to 1:600, more preferably from 1:0.4 to 1:35.

In one embodiment of the invention, the antimicrobial composition comprises 1,2-benzisothiazolin-3-one and caprylyl glycol. Preferably, a weight ratio of 1,2-benzisothiazolin-3-one to caprylyl glycol is from 1:0.5 to 1:100, more preferably from 1:0.7 to 1:67.

In one embodiment of the invention, the antimicrobial composition comprises 1,2-benzisothiazolin-3-one and chlorphenesin. Preferably, a weight ratio of 1,2-benzisothiazolin-3-one to chlorphenesin is from 1:20 to 1:600, more preferably from 1:20 to 1:50.

In one embodiment of the invention, the antimicrobial composition comprises 1,2-benzisothiazolin-3-one and 2,2'-dithiobis(N-methylbenzamide). Preferably, a weight ratio of 1,2-benzisothiazolin-3-one to 2,2'-dithiobis(N-methylbenzamide) is from 1:0.1 to 1:150, more preferably from 1:0.13 to 1:120.

In one embodiment of the invention, the antimicrobial composition comprises 1,2-benzisothiazolin-3-one and diazolidinyl urea. Preferably, a weight ratio of 1,2-benzisothiazolin-3-one to diazolidinyl urea is from 1:1 to 1:100.

In one embodiment of the invention, the antimicrobial composition comprises 1,2-benzisothiazolin-3-one and EDTA. Preferably, a weight ratio of 1,2-benzisothiazolin-3- one to EDTA is from 1:2 to 1:700, more preferably from 1:3 to 1:640, and most preferably from 1:3 to 1:500.

In one embodiment of the invention, the antimicrobial composition comprises 1,2-benzisothiazolin-3-one and ethylparaben. Preferably, a weight ratio of 1,2-benzisothiazolin-3-one to ethylparaben is from 1:10 to 1:500, more preferably from 1:13 to 1:400.

In one embodiment of the invention, the antimicrobial composition comprises 1,2-benzisothiazolin-3-one and imidazolidinyl urea. Preferably, a weight ratio of 1,2-benzisothiazolin-3-one to imidazolidinyl urea is from 1:20 to 1:30.

In one embodiment of the invention, the antimicrobial composition comprises 1,2-benzisothiazolin-3-one and methylparaben. Preferably, a weight ratio of 1,2-benzisothiazolin-3-one to methylparaben is from 1:1 to 1:300, more preferably from 1:3 to 1:240.

In one embodiment of the invention, the antimicrobial composition comprises 1,2-benzisothiazolin-3-one and phenoxyethanol. Preferably, a weight ratio of 1,2-benzisothiazolin-3-one to phenoxyethanol is from 1:1 to 1:1000, more preferably from 1:2.5 to 1:800.

In one embodiment of the invention, the antimicrobial composition comprises 1,2-benzisothiazolin-3-one and linoleamidopropyl PG-dimonium chloride phosphate. Preferably, a weight ratio of 1,2-benzisothiazolin-3-one to linoleamidopropyl PG-dimonium chloride phosphate is from 1:0.1 to 1:1000, more preferably from 1:0.5 to 1:800.

In one embodiment of the invention, the antimicrobial composition comprises 1,2-benzisothiazolin-3-one and cocamidopropyl PG-dimonium chloride phosphate. Preferably, a weight ratio of 1,2-benzisothiazolin-3-one to cocamidopropyl PG-dimonium chloride phosphate is from 1:1 to 1:1000, more preferably from 1:1.3 to 1:800.

In one embodiment of the invention, the antimicrobial composition comprises 1,2-benzisothiazolin-3-one and propylparaben. Preferably, a weight ratio of 1,2-benzisothiazolin-3-one to propylparaben is from 1:13 to 1:320.

In one embodiment of the invention, the antimicrobial composition comprises 1,2-benzisothiazolin-3-one and cis-1-(3-chloroallyl)-3,5,7-triaza-1-azoniaadamantane chloride. Preferably, a weight ratio of 1,2-benzisothiazolin-3-one to cis-1-(3-chloroallyl)-3,5,7-triaza-1-azoniaadamantane chloride is from 1:2 to 1:240, more preferably from 1:4 to 1:240.

In one embodiment of the invention, the antimicrobial composition comprises 1,2-benzisothiazolin-3-one and dehydroacetic acid or its salts, preferably sodium dehydroacetate. Preferably, a weight ratio of 1,2-benzisothiazolin-3-one to dehydroacetic acid or its salts is from 1:0.1 to 1:6, more preferably from 1:0.4 to 1:5.

In one embodiment of the invention, the antimicrobial composition comprises 1,2-benzisothiazolin-3-one and benzoic acid or its salts, preferably sodium benzoate. Preferably, a weight ratio of 1,2-benzisothiazolin-3-one to benzoic acid or its salts is from 1:1 to 1:2000, more preferably from 1:5 to 1:2000.

In one embodiment of the invention, the antimicrobial composition comprises 1,2-benzisothiazolin-3-one and sodium hydroxymethylglycinate. Preferably, a weight ratio of 1,2-benzisothiazolin-3-one to sodium hydroxymethylglycinate is from 1:20 to 1:150, more preferably from 1:27 to 1:100.

In one embodiment of the invention, the antimicrobial composition comprises 1,2-benzisothiazolin-3-one and zinc pyrithione. Preferably, a weight ratio of 1,2-benzisothiazolin-3-one to zinc pyrithione is from 1:0.01 to 1:7, more preferably from 1:0.04 to 1:6.

In one embodiment of the invention, the antimicrobial composition comprises 2-methyl-4-isothiazolin-3-one and caprylyl glycol. Preferably, a weight ratio of 2-methyl-4-isothiazolin-3-one to caprylyl glycol is from 1:0.5 to 1:267, more preferably from 1:0.5 to 1:20.

In one embodiment of the invention, the antimicrobial composition comprises 2-methyl-4-isothiazolin-3-one and chlorphenesin. Preferably, a weight ratio of 2-methyl-4-isothiazolin-3-one to chlorphenesin is from 1:0.5 to 1:700, more preferably from 1:1.2 to 1:600.

In one embodiment of the invention, the antimicrobial composition comprises 2-methyl-4-isothiazolin-3-one and hexamidine diisethionate. Preferably, a weight ratio of 2-methyl-4-isothiazolin-3-one to hexamidine diisethionate is from 1:0.0005 to 1:70, more preferably from 1:0.001 to 1:60.

In one embodiment of the invention, the antimicrobial composition comprises 2-methyl-4-isothiazolin-3-one and hexetidine. Preferably, a weight ratio of 2-methyl-4-isothiazolin-3-one to hexetidine is from 1:0.0005 to 1:280, more preferably from 1:0.002 to 1:250, and most preferably from 1:0.002 to 1:250.

In one embodiment of the invention, the antimicrobial composition comprises 2-methyl-4-isothiazolin-3-one and linoleamidopropyl PG-dimonium chloride phosphate. Preferably, a weight ratio of 2-methyl-4-isothiazolin-3-one to linoleamidopropyl PG-dimonium chloride phosphate is from 1:0.1 to 1:1600, more preferably from 1:0.2 to 1:1600, and most preferably from 1:0.3 to 1:600.

In one embodiment of the invention, the antimicrobial composition comprises 2-methyl-4-isothiazolin-3-one and cocamidopropyl PG-dimonium chloride phosphate. Preferably, a weight ratio of 2-methyl-4-isothiazolin-3-one to cocamidopropyl PG-dimonium chloride phosphate is from 1:0.03 to 1:90, and most preferably from 1:0.03 to 1:80.

In one embodiment of the invention, the antimicrobial composition comprises 2-methyl-4-isothiazolin-3-one and dehydroacetic acid or its salts, preferably sodium dehydroacetate. Preferably, a weight ratio of 2-methyl-4-isothiazolin-3-one to dehydroacetic acid or its salts is from 1:0.25 to 1:3.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

When a microbicide component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

A microbicide component also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and anti-corrosion additives.

When both microbicides are each first formulated with a solvent, the solvent used for the first microbicide may be the same as or different from the solvent used to formulate the other commercial microbicide, although water is preferred for most industrial biocide applications. It is preferred that the two solvents are miscible.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each may individual components may contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions onto, into, or at a locus subject to microbial attack. Suitable loci include, for example: industrial process water; electrocoat deposition systems,; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

Preferably, the microbicidal compositions of the present invention are used to inhibit the growth of microorganisms at a locus selected from one or more of mineral slurries, pulp and paper processing fluids and additives, starch, emulsions, dispersions, paints, latices, coatings, construction adhesives, such as ceramic adhesives, carpet backing adhesives, photographic chemicals, printing fluids, household products such as bathroom and kitchen cleaners, cosmetics, toiletries, shampoos, soaps, detergents, industrial cleaners, floor polishes, laundry rinse water, metal working fluids, textile products, agriculture adjuvant preservation, surfactant preservation, diagnostic reagent preservation, food preservation, and food, beverage, and industrial process pasteurizers.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 0.1 to 1,000 ppm of the isothiazoline ingredient of the composition in the locus. It is preferred that the isothiazolone ingredients of the composition be present in the locus in an amount of at least 0.5 ppm, more preferably at least 4 ppm and most preferably at least 10 ppm. It is preferred that the isothiazolone ingredients of the composition be present in the locus in an amount of no more than 1000 ppm, more preferably no more than 500 ppm, and most preferably no more than 200 ppm.

In one embodiment of the invention, the composition is substantially free of enzymatic biocides. Preferably, when BIT and either methylparaben or ethylparaben are combined, the composition is substantially free of enzymatic biocides. Enzymatic biocides are enzymes having activity against microbes, as defined, e.g., in U.S. Pat. App. Pub. No. 2002/0028754.

EXAMPLES

Materials and Methods

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index (``SI'')}$$

wherein:

$Q_A$=concentration of compound A (first component) in ppm, acting alone, which produced an end point (MIC of Compound A).

$Q_a$=concentration of compound A in ppm, in the mixture, which produced an end point.

$Q_B$=concentration of compound B (second component) in ppm, acting alone, which produced an end point (MIC of Compound B).

$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

Synergy tests were conducted using standard microtiter plate assays with media designed for optimal growth of the test microorganism. Soybean Casein Digest Broth (Tryptic Soy Broth, TSB medium) or minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides was tested by conducting high resolution MIC assays in the presence of various concentrations of MI. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient.

For MI combinations, the synergy of the combinations of the present invention was determined against two bacteria, *Escherichia coli* (*E. coli*—ATCC #8739) or *Pseudomonas aeruginosa* (*P. aeruginosa*—ATCC #15442), a yeast, *Candida albicans* (*C. albicans*—ATCC 10231), and a mold, *Aspergillus niger* (*A. niger*—ATCC 16404). The bacteria were used at a concentration of about $5 \times 10^6$ bacteria per mL and the yeast and mold at $5 \times 10^5$ fungi per mL. These microorganisms are representative of natural contaminants in many consumer and industrial applications. The plates were visually evaluated for microbial growth (turbidity) to determine the MIC after various incubation times at 25*C (yeast and mold) or 30° C. (bacteria).

For BIT combinations, the synergy of the combinations of the present invention was determined against a bacterium, *Pseudomonas aeruginosa* (*P. aeruginosa*—ATCC #15442), a yeast, *Candida albicans* (*C. albicans*—ATCC 10231), and a mold, *Aspergillus niger* (*A. niger*—ATCC 16404). The bacteria were used at a concentration of about $5 \times 10^6$ bacteria per mL and the yeast and mold at $5 \times 10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the MI combinations of the present invention are shown below in Tables 1 through 7. In each test, First Component (A) was MI and the Second Component (B) was the other commercial microbicide. Each table shows the specific combinations of MI and the second component; results against the microorganisms tested with incubation times; the end-point activity in ppm measured by the MIC for MI alone ($Q_A$), for the second component alone ($Q_B$), for MI in the mixture ($Q_a$) and for second component in the mixture ($Q_b$); the calculated SI value; and the range of synergistic ratios for each combination tested (MI/second component or A/B).

The test results for demonstration of synergy of the BIT combinations of the present invention are shown below in Tables 8 through 28. In each test, First Component (A) was BIT and the Second Component (B) was the other commercial microbicide. Each table shows the specific combinations of BIT and the second component; results against the microorganisms tested with incubation times; the end-point activity in ppm measured by the MIC for BIT alone ($Q_A$), for the second component alone ($Q_B$), for BIT in the mixture ($Q_a$) and for second component in the mixture ($Q_b$); the calculated SI value; and the range of synergistic ratios for each combination tested (BIT/second component or A/B).

TABLE 1

First Component (A) = 2-methyl-3-isothiazolone
Second Component (B) = Caprylyl glycol

| Microorganism | $Q_a$ | $Q_b$ | SI | A/B |
|---|---|---|---|---|
| *A. niger* 16404 - PDB | 0 | 3000 | 1.00 | — |
| (1 week) | 100 | 1000 | 0.53 | 1/10 |
|  | 100 | 2000 | 0.87 | 1/20 |
|  | 150 | 1000 | 0.63 | 1/6.7 |
|  | 150 | 2000 | 0.97 | 1/13 |
|  | 200 | 800 | 0.67 | 1/4 |
|  | 200 | 1000 | 0.73 | 1/5 |
|  | 300 | 600 | 0.80 | 1/2 |
|  | 300 | 800 | 0.87 | 1/2.6 |
|  | 300 | 1000 | 0.93 | 1/3.3 |
|  | 400 | 200 | 0.87 | 1/0.5 |
|  | 400 | 300 | 0.90 | 1/0.75 |
|  | 400 | 400 | 0.93 | 1/1 |
|  | 400 | 500 | 0.97 | 1/0.25 |
|  | 500 | 0 | 1.00 | — |
| *P. aeruginosa* 15442 - M9GY | 0 | 3000 | 1.00 | — |
| (48 hours) | 5 | 4000 | 1.58 | 1/800 |
|  | 10 | 4000 | 1.83 | 1/400 |
|  | 20 | 0 | 1.00 | — |
| *E. coli* 8739 - M9GY | 0 | 2000 | 1.00 | — |
| (24 hours) | 5 | 2000 | 1.17 | 1/400 |
|  | 7.5 | 2000 | 1.25 | 1/267 |
|  | 10 | 2000 | 1.33 | 1/200 |
|  | 30 | 0 | 1.00 | — |
| *C. albicans* 10231 - PDB | 0 | 2000 | 1.00 | — |
| (48 hours) | 40 | 2000 | 1.20 | 1/400 |
|  | 60 | 1000 | 0.80 | 1/267 |
|  | 60 | 2000 | 1.30 | 1/200 |
|  | 80 | 600 | 0.70 | 1/7.5 |
|  | 80 | 800 | 0.80 | 1/10 |
|  | 80 | 1000 | 0.90 | 1/12.5 |
|  | 100 | 500 | 0.75 | 1/5 |
|  | 100 | 600 | 0.80 | 1/6 |
|  | 100 | 800 | 0.90 | 1/8 |
|  | 100 | 1000 | 1.00 | 1/10 |
|  | 200 | 0 | 1.00 | — |

The synergistic ratios of MI/caprylyl glycol range from 1/0.5 to 1/267. The MI/caprylyl glycol combinations show enhanced control of mold and yeast.

TABLE 2

First Component (A) = 2-methyl-3-isothiazolone
Second Component (B) = Chlorphenesin

| Microorganism | $Q_a$ | $Q_b$ | SI | A/B |
|---|---|---|---|---|
| *A. niger* 16404 - PDB | 0 | 2000 | 1.00 | — |
| (4 days) | 100 | 2000 | 1.25 | 1/20 |
|  | 150 | 1000 | 0.88 | 1/6.7 |
|  | 150 | 2000 | 1.38 | 1/13.3 |
|  | 200 | 800 | 0.90 | 1/4 |
|  | 200 | 1000 | 1.00 | 1/5 |
|  | 300 | 600 | 1.05 | 1/2 |
|  | 400 | 0 | 1.00 | — |
| *P. aeruginosa* 15442 - M9GY | 0 | 4000 | 1.00 | — |
| (48 hours) | 5 | 4000 | 1.25 | 1/800 |
|  | 10 | 4000 | 1.50 | 1/400 |
|  | 20 | 0 | 1.00 | — |
| *E. coli* 8739 - M9GY | 0 | 2000 | 1.00 | — |
| (24 hours) | 5 | 2000 | 1.17 | 1/400 |
|  | 7.5 | 2000 | 1.25 | 1/267 |
|  | 10 | 2000 | 1.33 | 1/200 |
|  | 30 | 0 | 1.00 | — |
| *C. albicans* 10231 - PDB | 0 | 2000 | 1.00 | — |
| (24 hours) | 20 | 2000 | 1.10 | 1/100 |
|  | 40 | 800 | 0.60 | 1/20 |
|  | 40 | 1000 | 0.70 | 1/25 |
|  | 60 | 600 | 0.60 | 1/10 |
|  | 60 | 800 | 0.70 | 1/13 |
|  | 60 | 1000 | 0.80 | 1/17 |
|  | 80 | 400 | 0.60 | 1/5 |

TABLE 2-continued

First Component (A) = 2-methyl-3-isothiazolone
Second Component (B) = Chlorphenesin

| Microorganism | $Q_a$ | $Q_b$ | SI | A/B |
|---|---|---|---|---|
| | 80 | 500 | 0.65 | 1/6.25 |
| | 80 | 600 | 0.70 | 1/7.5 |
| | 80 | 800 | 0.80 | 1/10 |
| | 80 | 1000 | 0.90 | 1/12.5 |
| | 100 | 300 | 0.65 | 1/3 |
| | 100 | 400 | 0.70 | 1/4 |
| | 100 | 500 | 0.75 | 1/5 |
| | 100 | 600 | 0.80 | 1/6 |
| | 100 | 800 | 0.90 | 1/8 |
| | 100 | 1000 | 1.00 | 1/10 |
| | 200 | 0 | 1.00 | — |
| *P. aeruginosa* 15442 - TSB (48 hours) | 0 | 8000 | 1.00 | — |
| | 10 | 6000 | 0.92 | 1/600 |
| | 20 | 5000 | 0.96 | 1/250 |
| | 40 | 400 | 0.72 | 1/10 |
| | 40 | 600 | 0.74 | 1/15 |
| | 40 | 800 | 0.77 | 1/20 |
| | 40 | 1000 | 0.79 | 1/25 |
| | 40 | 2000 | 0.92 | 1/50 |
| | 50 | 60 | 0.84 | 1/1.2 |
| | 50 | 80 | 0.84 | 1/1.6 |
| | 50 | 100 | 0.85 | 1/2 |
| | 50 | 200 | 0.86 | 1/4 |
| | 50 | 300 | 0.87 | 1/6 |
| | 50 | 400 | 0.88 | 1/8 |
| | 50 | 500 | 0.90 | 1/10 |
| | 50 | 600 | 0.91 | 1/12 |
| | 50 | 800 | 0.93 | 1/16 |
| | 50 | 1000 | 0.96 | 1/20 |
| | 60 | 0 | 1.00 | — |
| *S. aureus* 6538 - TSB (48 hours) | 0 | 5000 | 1.00 | — |
| | 50 | 4000 | 0.97 | 1/80 |
| | 100 | 3000 | 0.93 | 1/30 |
| | 100 | 4000 | 1.13 | 1/40 |
| | 300 | 0 | 1.00 | — |

The synergistic ratios of MI/chlorphenesin range from 1/1.2 to 1/600. The MI/chlorphenesin combinations show enhanced control of yeast and bacteria.

TABLE 3

First Component (A) = 2-methyl-3-isothiazolone
Second Component (B) = Hexamidine diisethionate

| Microorganism | $Q_a$ | $Q_b$ | SI | A/B |
|---|---|---|---|---|
| *P. aeruginosa* 15442 - TSB (72 hours) | 0 | 2000 | 1.00 | — |
| | 5 | 100 | 0.32 | 1/20 |
| | 5 | 200 | 0.57 | 1/40 |
| | 5 | 300 | 0.82 | 1/60 |
| | 10 | 100 | 0.39 | 1/10 |
| | 10 | 200 | 0.64 | 1/20 |
| | 10 | 300 | 0.89 | 1/30 |
| | 20 | 40 | 0.39 | 1/2 |
| | 20 | 50 | 0.41 | 1/2.5 |
| | 20 | 60 | 0.44 | 1/3 |
| | 20 | 80 | 0.49 | 1/4 |
| | 20 | 100 | 0.54 | 1/5 |
| | 20 | 200 | 0.79 | 1/10 |
| | 30 | 60 | 0.58 | 1/2 |
| | 30 | 80 | 0.63 | 1/2.7 |
| | 30 | 100 | 0.68 | 1/3.3 |
| | 30 | 200 | 0.93 | 1/6.7 |
| | 40 | 40 | 0.67 | 1/1 |
| | 40 | 50 | 0.70 | 1/1.25 |
| | 40 | 60 | 0.72 | 1/1.5 |
| | 40 | 80 | 0.77 | 1/2 |
| | 40 | 100 | 0.82 | 1/2.5 |
| | 50 | 50 | 0.84 | 1/1 |
| | 50 | 60 | 0.86 | 1/1.2 |
| | 50 | 80 | 0.91 | 1/1.6 |

TABLE 3-continued

First Component (A) = 2-methyl-3-isothiazolone
Second Component (B) = Hexamidine diisethionate

| Microorganism | $Q_a$ | $Q_b$ | SI | A/B |
|---|---|---|---|---|
| | 50 | 100 | 0.96 | 1/2 |
| | 60 | 20 | 0.91 | 1/0.33 |
| | 60 | 30 | 0.93 | 1/0.5 |
| | 60 | 40 | 0.96 | 1/0.67 |
| | 60 | 50 | 0.98 | 1/0.83 |
| | 70 | 0 | 1.00 | — |
| *S. aureus* 6538 - TSB (72 hours) | 0 | 4000 | 1.00 | — |
| | 25 | 2 | 0.28 | 1/0.08 |
| | 25 | 3 | 0.38 | 1/0.12 |
| | 25 | 4 | 0.48 | 1/0.16 |
| | 25 | 5 | 0.58 | 1/0.2 |
| | 25 | 6 | 0.68 | 1/0.24 |
| | 25 | 8 | 0.88 | 1/0.32 |
| | 50 | 1 | 0.27 | 1/0.02 |
| | 50 | 2 | 0.37 | 1/0.04 |
| | 50 | 3 | 0.47 | 1/0.06 |
| | 50 | 4 | 0.57 | 1/0.08 |
| | 50 | 5 | 0.67 | 1/0.1 |
| | 50 | 6 | 0.77 | 1/0.12 |
| | 50 | 8 | 0.97 | 1/0.16 |
| | 75 | 0.6 | 0.31 | 1/0.008 |
| | 75 | 0.8 | 0.33 | 1/0.01 |
| | 75 | 1 | 0.35 | 1/0.01 |
| | 75 | 2 | 0.45 | 1/0.03 |
| | 75 | 3 | 0.55 | 1/0.04 |
| | 75 | 4 | 0.65 | 1/0.05 |
| | 75 | 5 | 0.75 | 1/0.07 |
| | 75 | 6 | 0.85 | 1/0.08 |
| | 100 | 0.5 | 0.38 | 1/0.005 |
| | 100 | 0.6 | 0.39 | 1/0.006 |
| | 100 | 0.8 | 0.41 | 1/0.008 |
| | 100 | 1 | 0.43 | 1/0.01 |
| | 100 | 2 | 0.53 | 1/0.02 |
| | 100 | 3 | 0.63 | 1/0.03 |
| | 100 | 4 | 0.73 | 1/0.04 |
| | 100 | 5 | 0.83 | 1/0.05 |
| | 100 | 6 | 0.93 | 1/0.06 |
| | 125 | 0.5 | 0.47 | 1/0.004 |
| | 125 | 0.6 | 0.48 | 1/0.005 |
| | 125 | 0.7 | 0.49 | 1/0.006 |
| | 125 | 0.8 | 0.50 | 1/0.006 |
| | 125 | 1 | 0.52 | 1/0.008 |
| | 125 | 2 | 0.62 | 1/0.016 |
| | 125 | 3 | 0.72 | 1/0.024 |
| | 125 | 4 | 0.82 | 1/0.032 |
| | 125 | 5 | 0.92 | 1/0.04 |
| | 150 | 0.4 | 0.54 | 1/0.003 |
| | 125 | 0.5 | 0.47 | 1/0.004 |
| | 125 | 0.6 | 0.48 | 1/0.0048 |
| | 125 | 0.8 | 0.50 | 1/0.0064 |
| | 125 | 1 | 0.52 | 1/0.008 |
| | 125 | 2 | 0.62 | 1/0.016 |
| | 125 | 3 | 0.72 | 1/0.024 |
| | 125 | 4 | 0.82 | 1/0.032 |
| | 125 | 5 | 0.92 | 1/0.04 |
| | 150 | 0.4 | 0.54 | 1/0.003 |
| | 150 | 0.5 | 0.55 | 1/0.003 |
| | 150 | 0.6 | 0.56 | 1/0.004 |
| | 150 | 0.8 | 0.58 | 1/0.005 |
| | 150 | 1 | 0.60 | 1/0.007 |
| | 150 | 2 | 0.70 | 1/0.013 |
| | 150 | 3 | 0.80 | 1/0.02 |
| | 150 | 4 | 0.90 | 1/0.03 |
| | 175 | 0.2 | 0.60 | 1/0.001 |
| | 175 | 0.3 | 0.61 | 1/0.002 |
| | 175 | 0.4 | 0.62 | 1/0.002 |
| | 175 | 0.5 | 0.63 | 1/0.003 |
| | 175 | 0.6 | 0.64 | 1/0.003 |
| | 175 | 0.8 | 0.66 | 1/0.004 |
| | 175 | 1 | 0.68 | 1/0.006 |
| | 175 | 2 | 0.78 | 1/0.011 |
| | 175 | 3 | 0.88 | 1/0.017 |
| | 175 | 4 | 0.98 | 1/0.03 |
| | 200 | 0.2 | 0.69 | 1/0.001 |

TABLE 3-continued

First Component (A) = 2-methyl-3-isothiazolone  
Second Component (B) = Hexamidine diisethionate

| Microorganism | $Q_a$ | $Q_b$ | SI | A/B |
|---|---|---|---|---|
| | 200 | 0.3 | 0.70 | 1/0.015 |
| | 200 | 0.4 | 0.71 | 1/0.002 |
| | 200 | 0.5 | 0.72 | 1/0.0025 |
| | 200 | 0.6 | 0.73 | 1/0.003 |
| | 200 | 0.8 | 0.75 | 1/0.004 |
| | 200 | 1 | 0.77 | 1/0.005 |
| | 200 | 2 | 0.87 | 1/0.01 |
| | 200 | 3 | 0.97 | 1/0.015 |
| | 300 | 0 | 1.00 | — |
| C. albicans 10231 - PDB (48 hours) | 0 | 2000 | 1.00 | — |
| | 50 | 40 | 0.75 | 1/0.8 |
| | 50 | 50 | 0.88 | 1/1 |
| | 100 | 5 | 0.56 | 1/0.05 |
| | 100 | 6 | 0.58 | 1/0.06 |
| | 100 | 8 | 0.60 | 1/0.08 |
| | 100 | 10 | 0.63 | 1/0.1 |
| | 100 | 20 | 0.75 | 1/0.2 |
| | 100 | 30 | 0.88 | 1/0.3 |
| | 125 | 2 | 0.65 | 1/0.16 |
| | 125 | 3 | 0.66 | 1/0.024 |
| | 125 | 4 | 0.68 | 1/0.032 |
| | 125 | 5 | 0.69 | 1/0.04 |
| | 125 | 6 | 0.70 | 1/0.048 |
| | 125 | 8 | 0.73 | 1/0.064 |
| | 125 | 10 | 0.75 | 1/0.08 |
| | 125 | 20 | 0.88 | 1/0.16 |
| | 150 | 2 | 0.78 | 1/0.01 |
| | 150 | 3 | 0.79 | 1/0.02 |
| | 150 | 4 | 0.80 | 1/0.03 |
| | 150 | 5 | 0.81 | 1/0.03 |
| | 150 | 6 | 0.83 | 1/0.04 |
| | 150 | 8 | 0.85 | 1/0.05 |
| | 150 | 10 | 0.88 | 1/0.07 |
| | 200 | 0 | 1 | — |

The synergistic ratios of MI/Hexamidine diisethionate range from 1/0.001 to 1/60. The MI/Hexamidine diisethionate combinations show enhanced control of yeast and bacteria.

TABLE 4

First Component (A) = 2-methyl-3-isothiazolone  
Second Component (B) = Hexetidine

| Microorganism | $Q_a$ | $Q_b$ | SI | A/B |
|---|---|---|---|---|
| P. aeruginosa 15442 - TSB (24 hours) | 0 | 10000 | 1.00 | — |
| | 10 | 10000 | 1.20 | 1/1000 |
| | 20 | 50 | 0.41 | 1/2.5 |
| | 20 | 60 | 0.41 | 1/3 |
| | 20 | 80 | 0.41 | 1/4 |
| | 20 | 100 | 0.41 | 1/5 |
| | 20 | 200 | 0.42 | 1/10 |
| | 20 | 300 | 0.43 | 1/15 |
| | 20 | 400 | 0.44 | 1/20 |
| | 20 | 500 | 0.45 | 1/25 |
| | 20 | 600 | 0.46 | 1/30 |
| | 20 | 800 | 0.48 | 1/40 |
| | 20 | 1000 | 0.50 | 1/50 |
| | 20 | 2000 | 0.60 | 1/100 |
| | 20 | 3000 | 0.70 | 1/150 |
| | 20 | 4000 | 0.80 | 1/200 |
| | 20 | 5000 | 0.90 | 1/250 |
| | 20 | 6000 | 1.00 | 1/300 |
| | 30 | 20 | 0.60 | 1/0.7 |
| | 30 | 30 | 0.60 | 1/1 |
| | 30 | 40 | 0.60 | 1/1 |
| | 30 | 50 | 0.61 | 1/7 |
| | 30 | 60 | 0.61 | 1/2 |
| | 30 | 80 | 0.61 | 1/3 |
| | 30 | 100 | 0.61 | 1/3 |
| | 30 | 200 | 0.62 | 1/7 |

TABLE 4-continued

First Component (A) = 2-methyl-3-isothiazolone  
Second Component (B) = Hexetidine

| Microorganism | $Q_a$ | $Q_b$ | SI | A/B |
|---|---|---|---|---|
| | 30 | 300 | 0.63 | 1/10 |
| | 30 | 400 | 0.64 | 1/13 |
| | 30 | 500 | 0.65 | 1/17 |
| | 30 | 600 | 0.66 | 1/20 |
| | 30 | 800 | 0.68 | 1/27 |
| | 30 | 1000 | 0.70 | 1/33 |
| | 30 | 2000 | 0.80 | 1/67 |
| | 30 | 3000 | 0.90 | 1/100 |
| | 30 | 4000 | 1.00 | 1/133 |
| | 40 | 20 | 0.80 | 1/0.5 |
| | 40 | 30 | 0.80 | 1/0.75 |
| | 40 | 40 | 0.80 | 1/1 |
| | 40 | 50 | 0.81 | 1/1.25 |
| | 40 | 60 | 0.81 | 1/1.5 |
| | 40 | 80 | 0.81 | 1/2 |
| | 40 | 100 | 0.81 | 1/2.5 |
| | 40 | 200 | 0.82 | 1/5 |
| | 40 | 300 | 0.83 | 1/7.5 |
| | 40 | 400 | 0.84 | 1/10 |
| | 40 | 500 | 0.85 | 1/12.5 |
| | 40 | 600 | 0.86 | 1/15 |
| | 40 | 800 | 0.88 | 1/20 |
| | 40 | 1000 | 0.90 | 1/25 |
| | 40 | 2000 | 1.00 | 1/50 |
| | 50 | 0 | 1.00 | — |
| S. aureus 6538 - TSB (48 hours) | 0 | 4 | 1.00 | — |
| | 25 | 3 | 0.83 | 1/0.12 |
| | 50 | 3 | 0.92 | 1/0.06 |
| | 75 | 2 | 0.75 | 1/0.03 |
| | 75 | 3 | 1.00 | 1/0.04 |
| | 100 | 2 | 0.83 | 1/0.02 |
| | 125 | 0.8 | 0.62 | 1/0.006 |
| | 125 | 1 | 0.67 | 1/0.008 |
| | 125 | 2 | 0.92 | 1/0.016 |
| | 150 | 0.8 | 0.70 | 1/0.005 |
| | 150 | 1 | 0.75 | 1/0.006 |
| | 150 | 2 | 1.00 | 1/0.01 |
| | 175 | 0.4 | 0.68 | 1/0.002 |
| | 175 | 0.5 | 0.71 | 1/0.003 |
| | 175 | 0.6 | 0.73 | 1/0.003 |
| | 175 | 0.8 | 0.78 | 1/0.005 |
| | 175 | 1 | 0.83 | 1/0.006 |
| | 175 | 2 | 1.08 | 1/0.01 |
| | 200 | 4 | 1.67 | 1/0.02 |
| | 300 | 0 | 1.00 | — |
| C. albicans 10231 - PDB (72 hours) | 0 | 2000 | 1.00 | — |
| | 50 | 20 | 0.58 | 1/0.4 |
| | 50 | 30 | 0.75 | 1/0.6 |
| | 50 | 40 | 0.92 | 1/0.8 |
| | 50 | 50 | 1.08 | 1/1 |
| | 100 | 6 | 0.60 | 1/0.06 |
| | 100 | 8 | 0.63 | 1/0.08 |
| | 100 | 10 | 0.67 | 1/0.1 |
| | 100 | 20 | 0.83 | 1/0.2 |
| | 100 | 30 | 1.00 | 1/0.3 |
| | 125 | 4 | 0.69 | 1/0.03 |
| | 125 | 5 | 0.71 | 1/0.04 |
| | 125 | 6 | 0.73 | 1/0.05 |
| | 125 | 8 | 0.76 | 1/0.06 |
| | 125 | 10 | 0.79 | 1/0.08 |
| | 125 | 20 | 0.96 | 1/0.16 |
| | 150 | 0.3 | 0.76 | 1/0.002 |
| | 150 | 0.4 | 0.76 | 1/0.003 |
| | 150 | 0.5 | 0.76 | 1/0.003 |
| | 150 | 0.6 | 0.76 | 1/0.004 |
| | 150 | 0.8 | 0.76 | 1/0.005 |
| | 150 | 1 | 0.77 | 1/0.006 |
| | 150 | 2 | 0.78 | 1/0.013 |
| | 150 | 3 | 0.80 | 1/0.02 |
| | 150 | 4 | 0.82 | 1/0.03 |
| | 150 | 5 | 0.83 | 1/0.03 |
| | 150 | 6 | 0.85 | 1/0.04 |
| | 150 | 8 | 0.88 | 1/0.05 |
| | 150 | 10 | 0.92 | 1/0.07 |

TABLE 4-continued

First Component (A) = 2-methyl-3-isothiazolone
Second Component (B) = Hexetidine

| Microorganism | $Q_a$ | $Q_b$ | SI | A/B |
|---|---|---|---|---|
| | 150 | 20 | 1.08 | 1/0.13 |
| | 200 | 0 | 1.00 | — |

The synergistic ratios of MI/Hexetidine range from 1/0.002 to 1/250. The MI/Hexetidine combinations show enhanced control of yeast and bacteria.

TABLE 5

First Component (A) = 2-methyl-3-isothiazolone
Second Component (B) = Linoleamidopropyl PG-dimonium chloride phosphate

| Microorganism | $Q_a$ | $Q_b$ | SI | A/B |
|---|---|---|---|---|
| A. niger 16404 - PDB (7 days) | 0 | 6000 | 1.00 | — |
| | 50 | 800 | 0.26 | 1/16 |
| | 50 | 1000 | 0.29 | 1/20 |
| | 50 | 2000 | 0.46 | 1/40 |
| | 50 | 3000 | 0.63 | 1/60 |
| | 50 | 4000 | 0.79 | 1/80 |
| | 50 | 5000 | 0.96 | 1/100 |
| | 75 | 600 | 0.29 | 1/8 |
| | 75 | 800 | 0.32 | 1/11 |
| | 75 | 1000 | 0.35 | 1/13 |
| | 75 | 2000 | 0.52 | 1/27 |
| | 75 | 3000 | 0.69 | 1/40 |
| | 75 | 4000 | 0.85 | 1/53 |
| | 75 | 5000 | 1.02 | 1/67 |
| | 100 | 500 | 0.33 | 1/5 |
| | 100 | 600 | 0.35 | 1/6 |
| | 100 | 800 | 0.38 | 1/8 |
| | 100 | 1000 | 0.42 | 1/10 |
| | 100 | 2000 | 0.58 | 1/20 |
| | 100 | 3000 | 0.75 | 1/30 |
| | 100 | 4000 | 0.92 | 1/40 |
| | 100 | 5000 | 1.08 | 1/50 |
| | 150 | 500 | 0.46 | 1/3 |
| | 150 | 600 | 0.48 | 1/5 |
| | 150 | 800 | 0.51 | 1/5 |
| | 150 | 1000 | 0.54 | 1/7 |
| | 150 | 2000 | 0.71 | 1/13 |
| | 150 | 3000 | 0.88 | 1/20 |
| | 150 | 4000 | 1.04 | 1/27 |
| | 200 | 400 | 0.57 | 1/2 |
| | 200 | 500 | 0.58 | 1/2.5 |
| | 200 | 600 | 0.60 | 1/3 |
| | 200 | 800 | 0.63 | 1/4 |
| | 200 | 1000 | 0.67 | 1/5 |
| | 200 | 2000 | 0.83 | 1/10 |
| | 200 | 3000 | 1.00 | 1/15 |
| | 300 | 80 | 0.76 | 1/0.3 |
| | 300 | 100 | 0.77 | 1/0.3 |
| | 300 | 200 | 0.78 | 1/0.7 |
| | 300 | 300 | 0.80 | 1/1 |
| | 300 | 400 | 0.82 | 1/1.3 |
| | 300 | 500 | 0.83 | 1/1.7 |
| | 300 | 600 | 0.85 | 1/2 |
| | 300 | 800 | 0.88 | 1/3 |
| | 300 | 1000 | 0.92 | 1/3 |
| | 300 | 2000 | 1.08 | 1.7 |
| | 400 | 0 | 1.00 | — |
| P. aeruginosa 15442 - M9GY (48 hours) | 0 | 10000 | 1.00 | — |
| | 5 | 4000 | 0.57 | 1/800 |
| | 5 | 5000 | 0.67 | 1/1000 |
| | 5 | 6000 | 0.77 | 1/1200 |
| | 5 | 8000 | 0.97 | 1/1600 |
| | 10 | 4000 | 0.73 | 1/400 |
| | 10 | 5000 | 0.83 | 1/500 |
| | 10 | 6000 | 0.93 | 1/600 |
| | 10 | 8000 | 1.13 | 1/800 |
| | 20 | 200 | 0.69 | 1/10 |
| | 20 | 300 | 0.70 | 1/15 |
| | 20 | 400 | 0.71 | 1/20 |
| | 20 | 500 | 0.72 | 1/25 |
| | 20 | 600 | 0.73 | 1/30 |
| | 20 | 800 | 0.75 | 1/40 |
| | 20 | 1000 | 0.77 | 1/50 |
| | 20 | 2000 | 0.87 | 1/100 |
| | 20 | 3000 | 0.97 | 1/150 |
| | 20 | 4000 | 1.07 | 1/200 |
| | 30 | 0 | 1.00 | — |
| P. aeruginosa 15442 - TSB (48 hours) | 0 | 10000 | 1.00 | — |
| | 20 | 10000 | 1.25 | 1/500 |
| | 30 | 300 | 0.41 | 1/10 |
| | 30 | 400 | 0.42 | 1/13 |
| | 30 | 500 | 0.43 | 1/17 |
| | 30 | 600 | 0.44 | 1/20 |
| | 30 | 800 | 0.46 | 1/27 |
| | 30 | 1000 | 0.48 | 1/33 |
| | 30 | 2000 | 0.58 | 1/67 |
| | 30 | 3000 | 0.68 | 1/100 |
| | 30 | 4000 | 0.78 | 1/133 |
| | 30 | 5000 | 0.88 | 1/167 |
| | 30 | 6000 | 0.98 | 1/200 |
| | 30 | 8000 | 1.18 | 1/267 |
| | 40 | 200 | 0.52 | 1/5 |
| | 40 | 300 | 0.53 | 1/7.5 |
| | 40 | 400 | 0.54 | 1/10 |
| | 40 | 500 | 0.55 | 1/12.5 |
| | 40 | 600 | 0.56 | 1/15 |
| | 40 | 800 | 0.58 | 1/20 |
| | 40 | 1000 | 0.60 | 1/25 |
| | 40 | 2000 | 0.70 | 1/50 |
| | 40 | 3000 | 0.80 | 1/75 |
| | 40 | 4000 | 0.90 | 1/100 |
| | 40 | 5000 | 1.00 | 1/125 |
| | 50 | 30 | 0.63 | 1/0.6 |
| | 50 | 40 | 0.63 | 1/0.8 |
| | 50 | 50 | 0.63 | 1/1 |
| | 50 | 60 | 0.63 | 1/1.2 |
| | 50 | 80 | 0.63 | 1/1.6 |
| | 50 | 100 | 0.64 | 1/2 |
| | 50 | 200 | 0.65 | 1/4 |
| | 50 | 300 | 0.66 | 1/6 |
| | 50 | 400 | 0.67 | 1/8 |
| | 50 | 500 | 0.68 | 1/10 |
| | 50 | 600 | 0.69 | 1/12 |
| | 50 | 800 | 0.71 | 1/16 |
| | 50 | 1000 | 0.73 | 1/20 |
| | 50 | 2000 | 0.83 | 1/40 |
| | 50 | 3000 | 0.93 | 1/60 |
| | 50 | 4000 | 1.03 | 1/80 |
| | 60 | 20 | 0.75 | 1/0.33 |
| | 60 | 30 | 0.75 | 1/0.5 |
| | 60 | 40 | 0.75 | 1/0.67 |
| | 60 | 50 | 0.76 | 1/0.8 |
| | 60 | 60 | 0.76 | 1/1 |
| | 60 | 80 | 0.76 | 1/1.3 |
| | 60 | 100 | 0.76 | 1/1.7 |
| | 60 | 200 | 0.77 | 1/3 |
| | 60 | 300 | 0.78 | 1/5 |
| | 60 | 400 | 0.79 | 1/7 |
| | 60 | 500 | 0.80 | 1/8 |
| | 60 | 600 | 0.81 | 1/10 |
| | 60 | 800 | 0.83 | 1/13 |
| | 60 | 1000 | 0.85 | 1/17 |
| | 60 | 2000 | 0.95 | 1/33 |
| | 60 | 3000 | 1.05 | 1/50 |
| | 80 | 0 | 1.00 | — |
| S. aureus 6538 - TSB (48 hours) | 0 | 40 | 1.00 | — |
| | 50 | 30 | 0.92 | 1/0.6 |
| | 50 | 40 | 1.17 | 1/0.8 |
| | 100 | 50 | 1.58 | 1/0.5 |
| | 200 | 20 | 1.17 | 1/0.1 |
| | 300 | 0 | 1.00 | — |

TABLE 5-continued

First Component (A) = 2-methyl-3-isothiazolone
Second Component (B) = Linoleamidopropyl
PG-dimonium chloride phosphate

| Microorganism | $Q_a$ | $Q_b$ | SI | A/B |
|---|---|---|---|---|
| C. albicans 10231 - PDB | 0 | 8000 | 1.00 | — |
| (24 hours) | 50 | 100 | 1.40 | 1/2 |
| | 100 | 100 | 1.80 | 1/1 |
| | 125 | 0 | 1.00 | — |

The synergistic ratios of MI/Linoleamidopropyl PG-dimonium chloride phosphate range from 1/0.3 to 1/1600. The MI/Linoleamidopropyl PG-dimonium chloride phosphate combinations show enhanced control of bacteria and mold.

TABLE 6

1st Component (A) = 2-methyl-3-isothiazolone; 2nd Component
(B) = Cocamidopropyl PG-dimonium chloride phosphate

| Microorganism | $Q_a$ | $Q_b$ | SI | A/B |
|---|---|---|---|---|
| A. niger 16404 - PDB | 0 | 1000 | 1.00 | — |
| (4 days) | 50 | 500 | 0.63 | 1/10 |
| | 50 | 600 | 0.73 | 1/12 |
| | 50 | 800 | 0.93 | 1/16 |
| | 50 | 1000 | 1.13 | 1/20 |
| | 75 | 400 | 0.59 | 1/5 |
| | 75 | 500 | 0.69 | 1/7 |
| | 75 | 600 | 0.79 | 1/8 |
| | 75 | 800 | 0.99 | 1/11 |
| | 100 | 300 | 0.55 | 1/3 |
| | 100 | 400 | 0.65 | 1/4 |
| | 100 | 500 | 0.75 | 1/5 |
| | 100 | 600 | 0.85 | 1/6 |
| | 100 | 800 | 1.05 | 1/8 |
| | 150 | 60 | 0.44 | 1/0.4 |
| | 150 | 80 | 0.46 | 1/0.5 |
| | 150 | 100 | 0.48 | 1/0.7 |
| | 150 | 200 | 0.58 | 1/1.3 |
| | 150 | 300 | 0.68 | 1/2 |
| | 150 | 400 | 0.78 | 1/3 |
| | 150 | 500 | 0.88 | 1/3 |
| | 150 | 600 | 0.98 | 1/4 |
| | 200 | 20 | 0.52 | 1/0.1 |
| | 200 | 30 | 0.53 | 1/0.15 |
| | 200 | 40 | 0.54 | 1/0.2 |
| | 200 | 50 | 0.55 | 1/0.25 |
| | 200 | 60 | 0.56 | 1/0.3 |
| | 200 | 80 | 0.58 | 1/0.4 |
| | 200 | 100 | 0.60 | 1/0.5 |
| | 200 | 200 | 0.70 | 1/1 |
| | 200 | 300 | 0.80 | 1/1.5 |
| | 200 | 400 | 0.90 | 1/2 |
| | 200 | 500 | 1.00 | 1/2.5 |
| | 300 | 20 | 0.77 | 1/0.07 |
| | 300 | 30 | 0.78 | 1/0.1 |
| | 300 | 40 | 0.79 | 1/0.13 |
| | 300 | 50 | 0.80 | 1/0.17 |
| | 300 | 60 | 0.81 | 1/0.2 |
| | 300 | 80 | 0.83 | 1/0.3 |
| | 300 | 100 | 0.85 | 1/0.3 |
| | 300 | 200 | 0.95 | 1/0.7 |
| | 300 | 300 | 1.05 | 1/1 |
| | 400 | 0 | 1.00 | — |
| P. aeruginosa 15442 - M9GY | 0 | 30 | 1.00 | — |
| (72 hours) | 10 | 30 | 1.33 | 1/3 |
| | 20 | 2 | 0.73 | 1/0.1 |
| | 20 | 3 | 0.77 | 1/0.15 |
| | 20 | 4 | 0.80 | 1/0.2 |
| | 20 | 5 | 0.83 | 1/0.25 |
| | 20 | 6 | 0.87 | 1/0.3 |
| | 20 | 8 | 0.93 | 1/0.4 |
| | 20 | 10 | 1.00 | 1/0.5 |
| | 30 | 0 | 1.00 | — |
| P. aeruginosa 15442 - TSB | 0 | 1000 | 1.00 | — |
| (48 hours) | 10 | 800 | 0.93 | 1/80 |
| | 10 | 1000 | 1.13 | 1/100 |
| | 20 | 600 | 0.85 | 1/30 |
| | 20 | 800 | 1.05 | 1/40 |
| | 30 | 500 | 0.88 | 1/17 |
| | 30 | 600 | 0.98 | 1/20 |
| | 30 | 800 | 1.18 | 1/27 |
| | 40 | 50 | 0.55 | 1/1.25 |
| | 40 | 60 | 0.56 | 1/1.5 |
| | 40 | 80 | 0.58 | 1/2 |
| | 40 | 100 | 0.60 | 1/2.5 |
| | 40 | 200 | 0.70 | 1/5 |
| | 40 | 300 | 0.80 | 1/7.5 |
| | 40 | 400 | 0.90 | 1/10 |
| | 40 | 500 | 1.00 | 1/12.5 |
| | 50 | 30 | 0.66 | 1/0.6 |
| | 50 | 40 | 0.67 | 1/0.8 |
| | 50 | 50 | 0.68 | 1/1 |
| | 50 | 60 | 0.69 | 1/1.2 |
| | 50 | 80 | 0.71 | 1/1.6 |
| | 50 | 100 | 0.73 | 1/2 |
| | 50 | 200 | 0.83 | 1/4 |
| | 50 | 300 | 0.93 | 1/6 |
| | 50 | 400 | 1.03 | 1/8 |
| | 60 | 6 | 0.76 | 1/0.1 |
| | 60 | 8 | 0.76 | 1/0.13 |
| | 60 | 10 | 0.76 | 1/0.17 |
| | 60 | 20 | 0.77 | 1/0.33 |
| | 60 | 30 | 0.78 | 1/0.5 |
| | 60 | 40 | 0.79 | 1/0.7 |
| | 60 | 50 | 0.80 | 1/0.8 |
| | 60 | 60 | 0.81 | 1/1 |
| | 60 | 80 | 0.83 | 1/1.3 |
| | 60 | 100 | 0.85 | 1/1.7 |
| | 60 | 200 | 0.95 | 1/3 |
| | 60 | 300 | 1.05 | 1/5 |
| | 80 | 0 | 1.00 | — |
| S. aureus 6538 - TSB | 0 | 30 | 1.00 | — |
| (24 hours) | 50 | 20 | 0.92 | 1/0.4 |
| | 100 | 10 | 0.83 | 1/0.1 |
| | 100 | 20 | 1.17 | 1/0.2 |
| | 125 | 8 | 0.89 | 1/0.06 |
| | 125 | 10 | 0.96 | 1/0.08 |
| | 125 | 20 | 1.29 | 1/0.16 |
| | 150 | 8 | 1.02 | 1/0.05 |
| | 200 | 0 | 1.00 | — |
| C. albicans 10231 - PDB | 0 | 100 | 1.00 | — |
| (24 hours) | 50 | 40 | 0.80 | 1/0.8 |
| | 50 | 50 | 0.90 | 1/1 |
| | 50 | 60 | 1.00 | 1/1.2 |
| | 100 | 3 | 0.83 | 1/0.03 |
| | 100 | 4 | 0.84 | 1/0.04 |
| | 100 | 5 | 0.85 | 1/0.05 |
| | 100 | 6 | 0.86 | 1/0.06 |
| | 100 | 8 | 0.88 | 1/0.08 |
| | 100 | 10 | 0.90 | 1/0.1 |
| | 100 | 20 | 1.00 | 1/0.2 |
| | 125 | 0 | 1.00 | — |

The synergistic ratios of MI/Cocamidopropyl PG-dimonium chloride phosphate range from 1/0.03 to 1/80. The MI/Cocamidopropyl PG-dimonium chloride phosphate combinations show enhanced control of bacteria, yeast and mold.

TABLE 7

First Component (A) = 2-methyl-3-isothiazolone
Second Component (B) = Sodium dehydroacetic acid

| Microorganism | $Q_a$ | $Q_b$ | SI | A/B |
|---|---|---|---|---|
| A. niger 16404 - PDB | 0 | 80 | 1.00 | — |
| (4 days) | 50 | 80 | 1.13 | 1/1.6 |
| | 75 | 40 | 0.69 | 1/0.5 |

TABLE 7-continued

First Component (A) = 2-methyl-3-isothiazolone
Second Component (B) = Sodium dehydroacetic acid

| Microorganism | $Q_a$ | $Q_b$ | SI | A/B |
|---|---|---|---|---|
| | 75 | 50 | 0.81 | 1/0.7 |
| | 75 | 60 | 0.94 | 1/0.8 |
| | 100 | 50 | 0.88 | 1/0.5 |
| | 100 | 60 | 1.00 | 1/0.6 |
| | 150 | 40 | 0.88 | 1/0.3 |
| | 150 | 50 | 1.00 | 1/0.3 |
| | 400 | 0 | 1.00 | — |
| P. aeruginosa 15442 - M9GY (48 hours) | 0 | 10000 | 1.00 | — |
| | 5 | 10000 | 1.17 | 1/2000 |
| | 10 | 10000 | 1.33 | 1/1000 |
| | 20 | 10000 | 1.67 | 1/500 |
| | 30 | 0 | 1.00 | — |
| E. coli 8739 - M9GY (24 hours) | 0 | 10000 | 1.00 | — |
| | 5 | 10000 | 1.17 | 1/2000 |
| | 10 | 10000 | 1.33 | 1/1000 |
| | 20 | 10000 | 1.67 | 1/500 |
| | 30 | 0 | 1.00 | — |
| C. albicans 10231 - PDB (24 hours) | 0 | 40 | 1.00 | — |
| | 10 | 30 | 0.80 | 1/3 |
| | 10 | 40 | 1.05 | 1/4 |
| | 20 | 30 | 0.85 | 1/1.5 |
| | 20 | 40 | 1.10 | 1/2 |
| | 60 | 20 | 0.80 | 1/0.3 |
| | 60 | 30 | 1.05 | 1/0.5 |
| | 80 | 20 | 0.90 | 1/0.25 |
| | 100 | 20 | 1.00 | 1/0.2 |
| | 200 | 0 | 1.00 | — |

The synergistic ratios of MI/sodium dehydroacetic acid range from 1/0.25 to 1/3. The MI/sodium dehydroacetic acid combinations show enhanced control of yeast and mold.

TABLE 8

First Component (A) = BIT
Second Component (B) = Benzalkonium chloride

| Microorganism | $Q_a$ | $Q_b$ | SI | A/B |
|---|---|---|---|---|
| A. niger 16404 - PDB (1 week) | 0 | 200 | 1.00 | — |
| | 2.5 | 80 | 0.48 | 1/32 |
| | 2.5 | 100 | 0.58 | 1/40 |
| | 2.5 | 200 | 1.08 | 1/80 |
| | 5 | 50 | 0.42 | 1/10 |
| | 5 | 60 | 0.47 | 1/12 |
| | 5 | 80 | 0.57 | 1/16 |
| | 5 | 100 | 0.67 | 1/20 |
| | 5 | 200 | 1.17 | 1/40 |
| | 10 | 40 | 0.53 | 1/4 |
| | 10 | 50 | 0.58 | 1/5 |
| | 10 | 60 | 0.63 | 1/6 |
| | 10 | 80 | 0.73 | 1/8 |
| | 10 | 100 | 0.83 | 1/10 |
| | 10 | 200 | 1.33 | 1/20 |
| | 15 | 8 | 0.54 | 1/0.5 |
| | 15 | 10 | 0.55 | 1/0.7 |
| | 15 | 20 | 0.60 | 1/1.3 |
| | 15 | 30 | 0.65 | 1/2 |
| | 15 | 40 | 0.70 | 1/3 |
| | 15 | 50 | 0.75 | 1/3 |
| | 15 | 60 | 0.80 | 1/4 |
| | 15 | 80 | 0.90 | 1/5 |
| | 15 | 100 | 1.00 | 1/7 |
| | 20 | 2 | 0.68 | 1/0.1 |
| | 20 | 3 | 0.68 | 1/0.15 |
| | 20 | 4 | 0.69 | 1/0.2 |
| | 20 | 5 | 0.69 | 1/0.25 |
| | 20 | 6 | 0.70 | 1/0.3 |
| | 20 | 8 | 0.71 | 1/0.4 |
| | 20 | 10 | 0.72 | 1/0.5 |
| | 20 | 20 | 0.77 | 1/1 |
| | 20 | 30 | 0.82 | 1/1.5 |
| | 20 | 40 | 0.87 | 1/2 |
| | 20 | 50 | 0.92 | 1/2.5 |
| | 20 | 60 | 0.97 | 1/3 |
| | 20 | 80 | 1.07 | 1/4 |
| | 20 | 100 | 1.17 | 1/5 |
| | 30 | 0 | 1.00 | — |
| P. aeruginosa 15442 - M9GY (48 hours) | 0 | 40 | 1.00 | — |
| | 10 | 30 | 0.85 | 1/3 |
| | 10 | 40 | 1.10 | 1/4 |
| | 20 | 20 | 0.70 | 1/1 |
| | 20 | 30 | 0.95 | 1/1.5 |
| | 20 | 40 | 1.20 | 1/2 |
| | 30 | 20 | 0.80 | 1/0.7 |
| | 30 | 30 | 1.05 | 1/1 |
| | 40 | 20 | 0.90 | 1/0.5 |
| | 40 | 30 | 1.15 | 1/0.75 |
| | 60 | 4 | 0.70 | 1/0.07 |
| | 60 | 5 | 0.73 | 1/0.08 |
| | 60 | 6 | 0.75 | 1/0.1 |
| | 60 | 8 | 0.80 | 1/0.13 |
| | 60 | 10 | 0.85 | 1/0.17 |
| | 60 | 20 | 1.10 | 1/0.3 |
| | 80 | 2 | 0.85 | 1/0.025 |
| | 80 | 3 | 0.88 | 1/0.04 |
| | 80 | 4 | 0.90 | 1/0.05 |
| | 80 | 5 | 0.93 | 1/0.06 |
| | 80 | 6 | 0.95 | 1/0.075 |
| | 80 | 8 | 1.00 | 1/0.1 |
| | 80 | 10 | 1.05 | 1/0.125 |
| | 100 | 0 | 1.00 | — |

The synergistic ratios of BIT/benzalkonium chloride range from 1/0.025 to 1/40. The BIT/benzalkonium chloride combinations show enhanced control of bacteria and mold.

TABLE 9

First Component (A) = BIT
Second Component (B) = Benzethonium chloride

| Microorganism | $Q_a$ | $Q_b$ | SI | A/B |
|---|---|---|---|---|
| A. niger 16404 - PDB (4 days) | 0 | 6 | 1.00 | — |
| | 2.5 | 4 | 0.75 | 1/1.6 |
| | 2.5 | 5 | 0.92 | 1/2 |
| | 2.5 | 6 | 1.08 | 1/2.4 |
| | 5 | 4 | 0.83 | 1/0.8 |
| | 5 | 5 | 1.00 | 1/1 |
| | 10 | 3 | 0.83 | 1/0.3 |
| | 10 | 4 | 1.00 | 1/0.4 |
| | 15 | 2 | 0.83 | 1/0.13 |
| | 15 | 3 | 1.00 | 1/0.2 |
| | 20 | 2 | 1.00 | 1/0.1 |
| | 30 | 0 | 1.00 | — |
| P. aeruginosa 15442 - M9GY (48 hours) | 0 | 40 | 1.00 | — |
| | 10 | 30 | 0.85 | 1/3 |
| | 10 | 40 | 1.10 | 1/4 |
| | 50 | 30 | 1.25 | 1/0.6 |
| | 100 | 0 | 1.00 | — |

The synergistic ratios of BIT/benzethonium chloride range from 1/0.13 to 1/3. The BIT/benzethonium chloride combinations show enhanced control of mold.

TABLE 10

First Component (A) = BIT
Second Component (B) = Benzyl alcohol

| Microorganism | $Q_a$ | $Q_b$ | SI | A/B |
|---|---|---|---|---|
| A. niger 16404 - PDB (1 week) | 0 | 5000 | 1.00 | — |
| | 10 | 5000 | 1.20 | 1/500 |
| | 20 | 4000 | 1.20 | 1/200 |
| | 30 | 30 | 0.61 | 1/1 |
| | 30 | 40 | 0.61 | 1/1.3 |
| | 30 | 50 | 0.61 | 1/1.7 |
| | 30 | 60 | 0.61 | 1/2 |
| | 30 | 80 | 0.62 | 1/3 |
| | 30 | 100 | 0.62 | 1/3 |
| | 30 | 200 | 0.64 | 1/7 |
| | 30 | 300 | 0.66 | 1/10 |
| | 30 | 400 | 0.68 | 1/13 |
| | 30 | 500 | 0.70 | 1/17 |
| | 30 | 600 | 0.72 | 1/20 |
| | 30 | 800 | 0.76 | 1/27 |
| | 30 | 1000 | 0.80 | 1/33 |
| | 30 | 2000 | 1.00 | 1/67 |
| | 50 | 0 | 1.00 | — |
| P. aeruginosa 15442 - M9GY (48 hours) | 0 | 200 | 1.00 | — |
| | 20 | 200 | 1.20 | 1/10 |
| | 30 | 100 | 0.80 | 1/3 |
| | 30 | 200 | 1.30 | 1/7 |
| | 40 | 80 | 0.80 | 1/2 |
| | 40 | 100 | 0.90 | 1/2.5 |
| | 40 | 200 | 1.40 | 1/5 |
| | 80 | 30 | 0.95 | 1/0.4 |
| | 100 | 0 | 1.00 | — |
| E. coli 8739 - M9GY (24 hours) | 0 | 4000 | 1.00 | — |
| | 2.5 | 4000 | 1.33 | 1/1600 |
| | 5 | 4000 | 1.67 | 1/800 |
| | 7.5 | 0 | 1.00 | — |
| C. albicans 10231 - PDB (48 hours) | 0 | 4000 | 1.00 | — |
| | 5 | 3000 | 0.92 | 1/600 |
| | 5 | 4000 | 1.17 | 1/800 |
| | 10 | 1000 | 0.58 | 1/100 |
| | 10 | 2000 | 0.83 | 1/200 |
| | 10 | 3000 | 1.08 | 1/300 |
| | 15 | 600 | 0.65 | 1/40 |
| | 15 | 800 | 0.70 | 1/53 |
| | 15 | 1000 | 0.75 | 1/67 |
| | 15 | 2000 | 1.00 | 1/133 |
| | 15 | 3000 | 1.25 | 1/200 |
| | 20 | 80 | 0.69 | 1/4 |
| | 20 | 100 | 0.69 | 1/5 |
| | 20 | 200 | 0.72 | 1/10 |
| | 20 | 300 | 0.74 | 1/15 |
| | 20 | 400 | 0.77 | 1/20 |
| | 20 | 500 | 0.79 | 1/25 |
| | 20 | 600 | 0.82 | 1/30 |
| | 20 | 800 | 0.87 | 1/40 |
| | 20 | 1000 | 0.92 | 1/50 |
| | 20 | 2000 | 1.17 | 1/100 |
| | 30 | 0 | 1.00 | — |

The synergistic ratios of BIT/benzyl alcohol range from 1/0.4 to 1/600. The BIT/benzyl alcohol combinations show enhanced control of bacteria, yeast and mold.

TABLE 11

First Component (A) = BIT
Second Component (B) = Caprylyl glycol

| Microorganism | $Q_a$ | $Q_b$ | SI | A/B |
|---|---|---|---|---|
| A. niger 16404 - PDB (1 week) | 0 | 2000 | 1.00 | — |
| | 5 | 2000 | 1.10 | 1/400 |
| | 10 | 1000 | 0.70 | 1/100 |
| | 10 | 2000 | 1.20 | 1/200 |
| | 15 | 1000 | 0.80 | 1/67 |
| | 15 | 2000 | 1.30 | 1/133 |
| | 30 | 20 | 0.61 | 1/0.7 |
| | 30 | 30 | 0.62 | 1/1 |
| | 30 | 40 | 0.62 | 1/1.3 |
| | 30 | 50 | 0.63 | 1/1.7 |
| | 30 | 60 | 0.63 | 1/2 |
| | 30 | 80 | 0.64 | 1/3 |
| | 30 | 100 | 0.65 | 1/3 |
| | 30 | 200 | 0.70 | 1/7 |
| | 30 | 300 | 0.75 | 1/10 |
| | 30 | 400 | 0.80 | 1/13 |
| | 30 | 500 | 0.85 | 1/17 |
| | 30 | 600 | 0.90 | 1/20 |
| | 30 | 800 | 1.00 | 1/27 |
| | 50 | 0 | 1.00 | — |
| P. aeruginosa 15442 - M9GY (24 hours) | 0 | 3000 | 1.00 | — |
| | 10 | 3000 | 1.10 | 1/300 |
| | 20 | 3000 | 1.20 | 1/150 |
| | 30 | 3000 | 1.30 | 1/100 |
| | 40 | 4000 | 1.73 | 1/100 |
| | 50 | 4000 | 1.83 | 1/80 |
| | 60 | 3000 | 1.60 | 1/50 |
| | 80 | 2000 | 1.47 | 1/25 |
| | 100 | 0 | 1.00 | — |
| E. coli 8739 - M9GY (24 hours) | 0 | 2000 | 1.00 | — |
| | 2.5 | 2000 | 1.33 | 1/800 |
| | 5 | 2000 | 1.67 | 1/400 |
| | 7.5 | 0 | 1.00 | — |
| C. albicans 10231 - PDB (24 hours) | 0 | 2000 | 1.00 | — |
| | 5 | 2000 | 1.17 | 1/400 |
| | 10 | 1000 | 0.83 | 1/100 |
| | 10 | 2000 | 1.33 | 1/200 |
| | 15 | 300 | 0.65 | 1/20 |
| | 15 | 400 | 0.70 | 1/27 |
| | 15 | 500 | 0.75 | 1/33 |
| | 15 | 600 | 0.80 | 1/40 |
| | 15 | 800 | 0.90 | 1/53 |
| | 15 | 1000 | 1.00 | 1/67 |
| | 20 | 200 | 0.77 | 1/10 |
| | 20 | 300 | 0.82 | 1/15 |
| | 20 | 400 | 0.87 | 1/20 |
| | 20 | 500 | 0.92 | 1/25 |
| | 20 | 600 | 0.97 | 1/30 |
| | 20 | 800 | 1.07 | 1/40 |
| | 30 | 0 | 1.00 | — |

The synergistic ratios of BIT/caprylyl glycol range from 1/0.7 to 1/100. The BIT/caprylyl glycol combinations show enhanced control of yeast and mold.

TABLE 12

First Component (A) = BIT
Second Component (B) = chlorphenesin

| Microorganism | $Q_a$ | $Q_b$ | SI | A/B |
|---|---|---|---|---|
| A. niger 16404 - PDB (1 week) | 0 | 2000 | 1.00 | — |
| | 2.5 | 2000 | 1.05 | 1/800 |
| | 5 | 2000 | 1.10 | 1/400 |
| | 10 | 2000 | 1.20 | 1/200 |
| | 15 | 1000 | 0.80 | 1/67 |
| | 15 | 2000 | 1.30 | 1/133 |
| | 20 | 500 | 0.65 | 1/25 |
| | 20 | 600 | 0.70 | 1/30 |
| | 20 | 800 | 0.80 | 1/40 |
| | 20 | 1000 | 0.90 | 1/50 |
| | 20 | 2000 | 1.40 | 1/100 |
| | 30 | 600 | 0.90 | 1/20 |
| | 30 | 800 | 1.00 | 1/27 |
| | 50 | 0 | 1.00 | — |
| P. aeruginosa 15442 - M9GY (72 hours) | 0 | 8000 | 1.00 | — |
| | 10 | 6000 | 0.85 | 1/600 |
| | 10 | 8000 | 1.10 | 1/800 |
| | 20 | 5000 | 0.83 | 1/250 |

TABLE 12-continued

First Component (A) = BIT
Second Component (B) = chlorphenesin

| Microorganism | $Q_a$ | $Q_b$ | SI | A/B |
|---|---|---|---|---|
| | 20 | 6000 | 0.95 | 1/300 |
| | 20 | 8000 | 1.20 | 1/400 |
| | 30 | 4000 | 0.80 | 1/133 |
| | 30 | 5000 | 0.93 | 1/167 |
| | 30 | 6000 | 1.05 | 1/200 |
| | 40 | 4000 | 0.90 | 1/100 |
| | 40 | 5000 | 1.03 | 1/125 |
| | 40 | 6000 | 1.15 | 1/150 |
| | 40 | 8000 | 1.40 | 1/200 |
| | 60 | 4000 | 1.10 | 1/67 |
| | 100 | 0 | 1.00 | — |

The synergistic ratios of BIT/Chlorphenesin range from 1/20 to 1/600. The BIT/Chlorphenesin combinations show enhanced control of bacteria and mold.

TABLE 13

First Component (A) = BIT
Second Component (B) = 2,2'-dithiobis(N-methylbenzamide)

| Microorganism | $Q_a$ | $Q_b$ | SI | A/B |
|---|---|---|---|---|
| A. niger 16404 - PDB | 0 | 1000 | 1.00 | — |
| (3 days) | 2.5 | 1000 | 1.13 | 1/400 |
| | 5 | 400 | 0.65 | 1/80 |
| | 5 | 500 | 0.75 | 1/100 |
| | 5 | 600 | 0.85 | 1/120 |
| | 5 | 800 | 1.05 | 1/160 |
| | 10 | 100 | 0.60 | 1/10 |
| | 10 | 200 | 0.70 | 1/20 |
| | 10 | 300 | 0.80 | 1/30 |
| | 10 | 400 | 0.90 | 1/40 |
| | 10 | 500 | 1.00 | 1/50 |
| | 15 | 2 | 0.75 | 1/0.13 |
| | 15 | 4 | 0.75 | 1/0.3 |
| | 15 | 5 | 0.76 | 1/0.3 |
| | 15 | 6 | 0.76 | 1/0.4 |
| | 15 | 8 | 0.76 | 1/0.5 |
| | 15 | 10 | 0.76 | 1/0.7 |
| | 15 | 20 | 0.77 | 1/1.3 |
| | 15 | 30 | 0.78 | 1/2 |
| | 15 | 40 | 0.79 | 1/3 |
| | 15 | 50 | 0.80 | 1/3 |
| | 15 | 60 | 0.81 | 1/4 |
| | 15 | 80 | 0.83 | 1/5 |
| | 15 | 100 | 0.85 | 1/7 |
| | 15 | 200 | 0.95 | 1/13 |
| | 15 | 300 | 1.05 | 1/20 |
| | 20 | 0 | 1.00 | — |
| P. aeruginosa 15442 - M9GY | 0 | 200 | 1.00 | — |
| (48 hours) | 20 | 200 | 1.20 | 1/10 |
| | 30 | 100 | 0.80 | 1/3 |
| | 30 | 200 | 1.30 | 1/7 |
| | 40 | 80 | 0.80 | 1/2 |
| | 40 | 100 | 0.90 | 1/2.5 |
| | 40 | 200 | 1.40 | 1/5 |
| | 100 | 0 | 1.00 | — |

The synergistic ratios of BIT/2,2'-dithiobis(N-methylbenzamide) range from 1/0.13 to 1/120. The BIT/2,2'-dithiobis(N-methylbenzamide) combinations show enhanced control of bacteria and mold.

TABLE 14

First Component (A) = BIT
Second Component (B) = Diazolidinyl urea

| Microorganism | $Q_a$ | $Q_b$ | SI | A/B |
|---|---|---|---|---|
| A. niger 16404 - PDB | 0 | 1000 | 1.00 | — |
| (3 days) | 10 | 1000 | 1.50 | 1/100 |
| | 15 | 400 | 1.15 | 1/27 |
| | 20 | 0 | 1.00 | — |
| P. aeruginosa 15442 - M9GY | 0 | 80 | 1.00 | — |
| (48 hours) | 20 | 60 | 0.95 | 1/3 |
| | 40 | 40 | 0.90 | 1/1 |
| | 40 | 50 | 1.03 | 1/1.25 |
| | 60 | 30 | 0.98 | 1/0.5 |
| | 80 | 30 | 1.18 | 1/0.375 |
| | 100 | 0 | 1.00 | — |
| E. coli 8739 - M9GY | 0 | 100 | 1.00 | — |
| (48 hours) | 1 | 100 | 0.63 | 1/100 |
| | 1 | 200 | 1.13 | 1/200 |
| | 2 | 100 | 0.75 | 1/50 |
| | 2 | 200 | 1.25 | 1/100 |
| | 4 | 80 | 0.90 | 1/20 |
| | 4 | 100 | 1.00 | 1/25 |
| | 8 | 0 | 1.00 | — |
| C. albicans 10231 - PDB | 0 | 2000 | 1.00 | — |
| (24 hours) | 10 | 2000 | 1.33 | 1/200 |
| | 15 | 800 | 0.90 | 1/53 |
| | 15 | 1000 | 1.00 | 1/67 |
| | 20 | 600 | 0.97 | 1/30 |
| | 20 | 800 | 1.07 | 1/40 |
| | 30 | 0 | 1.00 | — |

The synergistic ratios of BIT/Diazolidinyl urea range from 1/1 to 1/100. The BIT/Diazolidinyl urea combinations show enhanced control of bacteria.

TABLE 15

First Component (A) = BIT
Second Component (B) = EDTA

| Microorganism | $Q_a$ | $Q_b$ | SI | A/B |
|---|---|---|---|---|
| A. niger 16404 - PDB | 0 | 2000 | 1.00 | — |
| (4 days) | 2.5 | 1200 | 0.73 | 1/480 |
| | 2.5 | 1600 | 0.93 | 1/640 |
| | 2.5 | 2000 | 1.13 | 1/800 |
| | 5 | 800 | 0.65 | 1/160 |
| | 5 | 1000 | 0.75 | 1/200 |
| | 5 | 1200 | 0.85 | 1/240 |
| | 5 | 1600 | 1.05 | 1/320 |
| | 10 | 60 | 0.53 | 1/6 |
| | 10 | 80 | 0.54 | 1/8 |
| | 10 | 100 | 0.55 | 1/10 |
| | 10 | 120 | 0.56 | 1/12 |
| | 10 | 160 | 0.58 | 1/16 |
| | 10 | 200 | 0.60 | 1/20 |
| | 10 | 400 | 0.70 | 1/40 |
| | 10 | 600 | 0.80 | 1/60 |
| | 10 | 800 | 0.90 | 1/80 |
| | 10 | 1000 | 1.00 | 1/100 |
| | 15 | 40 | 0.77 | 1/3 |
| | 15 | 60 | 0.78 | 1/4 |
| | 15 | 80 | 0.79 | 1/5 |
| | 15 | 100 | 0.80 | 1/7 |
| | 15 | 120 | 0.81 | 1/8 |
| | 15 | 160 | 0.83 | 1/11 |
| | 15 | 200 | 0.85 | 1/13 |
| | 15 | 400 | 0.95 | 1/27 |
| | 15 | 600 | 1.05 | 1/40 |
| | 20 | 0 | 1.00 | — |

The synergistic ratios of BIT/EDTA range from 1/3 to 1/640. The BIT/EDTA combinations show enhanced control of mold.

TABLE 16

First Component (A) = BIT
Second Component (B) = ethylparaben

| Microorganism | $Q_a$ | $Q_b$ | SI | A/B |
|---|---|---|---|---|
| A. niger 16404 - PDB | 0 | 2000 | 1.00 | — |
| (3 days) | 2.5 | 200 | 0.23 | 1/80 |
| | 2.5 | 300 | 0.28 | 1/120 |
| | 2.5 | 400 | 0.33 | 1/160 |
| | 2.5 | 500 | 0.38 | 1/200 |
| | 2.5 | 600 | 0.43 | 1/240 |
| | 2.5 | 800 | 0.53 | 1/320 |
| | 2.5 | 1000 | 0.63 | 1/400 |
| | 2.5 | 2000 | 1.13 | 1/800 |
| | 5 | 600 | 0.55 | 1/120 |
| | 5 | 800 | 0.65 | 1/160 |
| | 5 | 1000 | 0.75 | 1/200 |
| | 5 | 2000 | 1.25 | 1/400 |
| | 10 | 400 | 0.70 | 1/40 |
| | 5 | 500 | 0.50 | 1/100 |
| | 5 | 600 | 0.55 | 1/120 |
| | 5 | 800 | 0.65 | 1/160 |
| | 5 | 1000 | 0.75 | 1/200 |
| | 5 | 2000 | 1.25 | 1/400 |
| | 15 | 200 | 0.85 | 1/13 |
| | 15 | 300 | 0.90 | 1/20 |
| | 15 | 400 | 0.95 | 1/27 |
| | 15 | 500 | 1.00 | 1/33 |
| | 20 | 0 | 1.00 | — |
| P. aeruginosa 15442 - M9GY | 0 | 3000 | 1.00 | — |
| (48 hours) | 10 | 2000 | 0.77 | 1/200 |
| | 10 | 3000 | 1.10 | 1/300 |
| | 20 | 2000 | 0.87 | 1/100 |
| | 20 | 3000 | 1.20 | 1/150 |
| | 40 | 2000 | 1.07 | 1/50 |
| | 100 | 0 | 1.00 | — |

The synergistic ratios of BIT/ethylparaben range from 1/13 to 1/400. The BIT/ethylparaben combinations show enhanced control of bacteria and mold.

TABLE 17

First Component (A) = BIT
Second Component (B) = glutaraldehyde

| Microorganism | $Q_a$ | $Q_b$ | SI | A/B |
|---|---|---|---|---|
| A. niger 16404 - PDB | 0 | 400 | 1.00 | — |
| (3 days) | 10 | 500 | 1.75 | 1/50 |
| | 15 | 400 | 1.75 | 1/27 |
| | 20 | 0 | 1.00 | — |
| P. aeruginosa 15442 - M9GY | 0 | 60 | 1.00 | — |
| (48 hours) | 20 | 40 | 1.00 | 1/2 |
| | 40 | 40 | 1.33 | 1/1 |
| | 60 | 0 | 1.00 | — |
| E. coli 8739 - M9GY | 0 | 50 | 1.00 | — |
| (24 hours) | 2.5 | 40 | 1.05 | 1/16 |
| | 5 | 40 | 1.30 | 1/8 |
| | 7.5 | 20 | 1.15 | 1/3 |
| | 10 | 0 | 1.00 | — |
| C. albicans 10231 - PDB | 0 | 30 | 1.00 | — |
| (24 hours) | 5 | 40 | 1.50 | 1/8 |
| | 10 | 30 | 1.33 | 1/3 |
| | 15 | 30 | 1.50 | 1/2 |
| | 20 | 20 | 1.33 | 1/1 |
| | 30 | 0 | 1.00 | — |

The BIT/glutaraldehyde combinations did not show synergy in this test.

TABLE 18

First Component (A) = BIT
Second Component (B) = Imidalozidinyl urea

| Microorganism | $Q_a$ | $Q_b$ | SI | A/B |
|---|---|---|---|---|
| A. niger 16404 - PDB | 0 | 8000 | 1.00 | — |
| (3 days) | 10 | 5000 | 1.13 | 1/500 |
| | 15 | 3000 | 1.13 | 1/200 |
| | 20 | 0 | 1.00 | — |
| P. aeruginosa 15442 - M9GY | 0 | 400 | 1.00 | — |
| (48 hours) | 10 | 300 | 0.85 | 1/30 |
| | 10 | 400 | 1.10 | 1/40 |
| | 40 | 300 | 1.15 | 1/7.5 |
| | 80 | 100 | 1.05 | 1/1.25 |
| | 100 | 0 | 1.00 | — |
| E. coli 8739 - M9GY | 0 | 400 | 1.00 | — |
| (48 hours) | 2.5 | 300 | 1.08 | 1/120 |
| | 5 | 100 | 0.92 | 1/20 |
| | 5 | 200 | 1.17 | 1/40 |
| | 7.5 | 0 | 1.00 | — |
| C. albicans 10231 - PDB | 0 | 10000 | 1.00 | — |
| (24 hours) | 5 | 8000 | 0.97 | 1/1600 |
| | 10 | 8000 | 1.13 | 1/800 |
| | 15 | 4000 | 0.90 | 1/267 |
| | 15 | 5000 | 1.00 | 1/333 |
| | 20 | 4000 | 1.07 | 1/200 |
| | 30 | 0 | 1.00 | — |

The synergistic ratios of BIT/Imidalozidinyl urea range from 1/20 to 1/30. The BIT/Imidalozidinyl urea combinations show enhanced control of bacteria and yeast.

TABLE 19

First Component (A) = BIT
Second Component (B) = methylparaben

| Microorganism | $Q_a$ | $Q_b$ | SI | A/B |
|---|---|---|---|---|
| A. niger 16404 - PDB | 0 | 800 | 1.00 | — |
| (4 days) | 2.5 | 600 | 0.83 | 1/240 |
| | 2.5 | 800 | 1.08 | 1/320 |
| | 5 | 500 | 0.79 | 1/100 |
| | 5 | 600 | 0.92 | 1/120 |
| | 5 | 800 | 1.17 | 1/160 |
| | 10 | 400 | 0.83 | 1/40 |
| | 10 | 500 | 0.96 | 1/50 |
| | 10 | 600 | 1.08 | 1/60 |
| | 20 | 200 | 0.92 | 1/10 |
| | 20 | 300 | 1.04 | 1/15 |
| | 30 | 0 | 1.00 | — |
| P. aeruginosa 15442 - M9GY | 0 | 3000 | 1.00 | — |
| (48 hours) | 10 | 2000 | 0.77 | 1/200 |
| | 10 | 3000 | 1.10 | 1/300 |
| | 20 | 2000 | 0.87 | 1/100 |
| | 20 | 3000 | 1.20 | 1/150 |
| | 50 | 1000 | 0.83 | 1/20 |
| | 50 | 2000 | 1.17 | 1/40 |
| | 60 | 800 | 0.87 | 1/13 |
| | 60 | 1000 | 0.93 | 1/17 |
| | 60 | 200 | 0.67 | 1/3 |
| | 80 | 600 | 1.00 | 1/7.5 |
| | 100 | 0 | 1.00 | — |

The synergistic ratios of BIT/methylparaben range from 1/3 to 1/240. The BIT/methylparaben combinations show enhanced control of bacteria and mold.

TABLE 20

First Component (A) = BIT
Second Component (B) = phenoxyethanol

| Microorganism | $Q_a$ | $Q_b$ | SI | A/B |
|---|---|---|---|---|
| A. niger 16404 - PDB | 0 | 3000 | 1.00 | — |
| (3 days) | 2.5 | 2000 | 0.79 | 1/800 |

TABLE 20-continued

First Component (A) = BIT
Second Component (B) = phenoxyethanol

| Microorganism | $Q_a$ | $Q_b$ | SI | A/B |
|---|---|---|---|---|
|  | 2.5 | 3000 | 1.13 | 1/1200 |
|  | 5 | 2000 | 0.92 | 1/400 |
|  | 5 | 3000 | 1.25 | 1/600 |
|  | 10 | 2000 | 1.17 | 1/200 |
|  | 20 | 0 | 1.00 | — |
| *P. aeruginosa* 15442 - M9GY | 0 | 3000 | 1.00 | — |
| (48 hours) | 10 | 3000 | 1.10 | 1/300 |
|  | 20 | 2000 | 0.87 | 1/100 |
|  | 20 | 3000 | 1.20 | 1/150 |
|  | 50 | 500 | 0.67 | 1/10 |
|  | 50 | 600 | 0.70 | 1/12 |
|  | 50 | 700 | 0.73 | 1/14 |
|  | 50 | 800 | 0.77 | 1/16 |
|  | 50 | 900 | 0.80 | 1/18 |
|  | 50 | 1000 | 0.83 | 1/20 |
|  | 50 | 2000 | 1.17 | 1/40 |
|  | 60 | 1000 | 0.93 | 1/17 |
|  | 60 | 2000 | 1.27 | 1/33 |
|  | 80 | 200 | 0.87 | 1/2.5 |
|  | 80 | 300 | 0.90 | 1/3.75 |
|  | 80 | 400 | 0.93 | 1/5 |
|  | 80 | 500 | 0.97 | 1/6.25 |
|  | 80 | 600 | 1.00 | 1/7.5 |
|  | 100 | 0 | 1.00 | — |

The synergistic ratios of BIT/phenoxyethanol range from 1/2.5 to 1/800. The BIT/phenoxyethanol combinations show enhanced control of bacteria and mold.

TABLE 21

First Component (A) = BIT
Second Component (B) = Linoleamidopropyl PG-dimonium chloride phosphate

| Microorganism | $Q_a$ | $Q_b$ | SI | A/B |
|---|---|---|---|---|
| *A. niger* 16404 - PDB | 0 | 3000 | 1.00 | — |
| (4 days) | 2.5 | 800 | 0.35 | 1/320 |
|  | 2.5 | 1000 | 0.42 | 1/400 |
|  | 2.5 | 2000 | 0.75 | 1/800 |
|  | 2.5 | 3000 | 1.08 | 1/1200 |
|  | 5 | 600 | 0.37 | 1/120 |
|  | 5 | 800 | 0.43 | 1/160 |
|  | 5 | 1000 | 0.50 | 1/200 |
|  | 5 | 2000 | 0.83 | 1/400 |
|  | 5 | 3000 | 1.17 | 1/600 |
|  | 10 | 500 | 0.50 | 1/50 |
|  | 10 | 600 | 0.53 | 1/60 |
|  | 10 | 800 | 0.60 | 1/80 |
|  | 10 | 1000 | 0.67 | 1/100 |
|  | 10 | 2000 | 1.00 | 1/200 |
|  | 15 | 80 | 0.53 | 1/5 |
|  | 15 | 100 | 0.53 | 1/7 |
|  | 15 | 200 | 0.57 | 1/13 |
|  | 15 | 300 | 0.60 | 1/20 |
|  | 15 | 400 | 0.63 | 1/27 |
|  | 15 | 500 | 0.67 | 1/33 |
|  | 15 | 600 | 0.70 | 1/40 |
|  | 15 | 800 | 0.77 | 1/53 |
|  | 15 | 1000 | 0.83 | 1/67 |
|  | 15 | 2000 | 1.17 | 1/133 |
|  | 20 | 20 | 0.67 | 1/1 |
|  | 20 | 30 | 0.68 | 1/1.5 |
|  | 20 | 40 | 0.68 | 1/2 |
|  | 20 | 50 | 0.68 | 1/2.5 |
|  | 20 | 60 | 0.69 | 1/3 |
|  | 20 | 80 | 0.69 | 1/4 |
|  | 20 | 100 | 0.70 | 1/5 |
|  | 20 | 200 | 0.73 | 1/10 |
|  | 20 | 300 | 0.77 | 1/15 |
|  | 20 | 400 | 0.80 | 1/20 |

TABLE 21-continued

First Component (A) = BIT
Second Component (B) = Linoleamidopropyl PG-dimonium chloride phosphate

| Microorganism | $Q_a$ | $Q_b$ | SI | A/B |
|---|---|---|---|---|
|  | 20 | 500 | 0.83 | 1/25 |
|  | 20 | 600 | 0.87 | 1/30 |
|  | 20 | 800 | 0.93 | 1/40 |
|  | 20 | 1000 | 1.00 | 1/50 |
|  | 30 | 0 | 1.00 | — |
| *P. aeruginosa* 15442 - M9GY | 0 | 10000 | 1.00 | — |
| (48 hours) | 10 | 3000 | 0.40 | 1/300 |
|  | 10 | 4000 | 0.50 | 1/400 |
|  | 10 | 5000 | 0.60 | 1/500 |
|  | 10 | 6000 | 0.70 | 1/600 |
|  | 10 | 7000 | 0.80 | 1/700 |
|  | 10 | 8000 | 0.90 | 1/800 |
|  | 10 | 10000 | 1.10 | 1/1000 |
|  | 20 | 3000 | 0.50 | 1/150 |
|  | 20 | 4000 | 0.60 | 1/200 |
|  | 20 | 5000 | 0.70 | 1/250 |
|  | 20 | 6000 | 0.80 | 1/300 |
|  | 20 | 7000 | 0.90 | 1/350 |
|  | 20 | 8000 | 1.00 | 1/400 |
|  | 30 | 5000 | 0.80 | 1/167 |
|  | 30 | 6000 | 0.90 | 1/200 |
|  | 30 | 8000 | 1.10 | 1/267 |
|  | 40 | 3000 | 0.70 | 1/75 |
|  | 40 | 4000 | 0.80 | 1/100 |
|  | 40 | 5000 | 0.90 | 1/125 |
|  | 40 | 6000 | 1.00 | 1/150 |
|  | 60 | 600 | 0.66 | 1/10 |
|  | 60 | 800 | 0.68 | 1/13 |
|  | 60 | 1000 | 0.70 | 1/17 |
|  | 60 | 2000 | 0.80 | 1/33 |
|  | 60 | 3000 | 0.90 | 1/50 |
|  | 60 | 4000 | 1.00 | 1/67 |
|  | 80 | 40 | 0.80 | 1/0.5 |
|  | 80 | 50 | 0.81 | 1/0.625 |
|  | 80 | 60 | 0.81 | 1/0.75 |
|  | 80 | 80 | 0.81 | 1/1 |
|  | 80 | 100 | 0.81 | 1/1.25 |
|  | 80 | 200 | 0.82 | 1/2.5 |
|  | 80 | 300 | 0.83 | 1/3.75 |
|  | 80 | 400 | 0.84 | 1/5 |
|  | 80 | 500 | 0.85 | 1/6.25 |
|  | 80 | 600 | 0.86 | 1/7.5 |
|  | 80 | 800 | 0.88 | 1/10 |
|  | 80 | 1000 | 0.90 | 1/12.5 |
|  | 80 | 2000 | 1.00 | 1/25 |
|  | 100 | 0 | 1.00 | — |

The synergistic ratios of BIT/Linoleamidopropyl PG-dimonium chloride phosphate range from 1/0.5 to 1/800. The BIT/Linoleamidopropyl PG-dimonium chloride phosphate combinations show enhanced control of bacteria and mold.

TABLE 22

First Component (A) = BIT
Second Component (B) = Cocamidopropyl PG-dimonium chloride phosphate

| Microorganism | $Q_a$ | $Q_b$ | SI | A/B |
|---|---|---|---|---|
| *A. niger* 16404 - PDB | 0 | 3000 | 1.00 | — |
| (1 week) | 2.5 | 500 | 0.25 | 1/200 |
|  | 2.5 | 600 | 0.28 | 1/240 |
|  | 2.5 | 800 | 0.35 | 1/320 |
|  | 2.5 | 1000 | 0.42 | 1/400 |
|  | 2.5 | 2000 | 0.75 | 1/800 |
|  | 2.5 | 3000 | 1.08 | 1/1200 |
|  | 5 | 600 | 0.37 | 1/120 |
|  | 5 | 800 | 0.43 | 1/160 |
|  | 5 | 1000 | 0.50 | 1/200 |
|  | 5 | 2000 | 0.83 | 1/400 |

TABLE 22-continued

First Component (A) = BIT
Second Component (B) = Cocamidopropyl PG-dimonium chloride phosphate

| Microorganism | $Q_a$ | $Q_b$ | SI | A/B |
|---|---|---|---|---|
| | 5 | 3000 | 1.17 | 1/600 |
| | 10 | 60 | 0.35 | 1/6 |
| | 10 | 80 | 0.36 | 1/8 |
| | 10 | 100 | 0.37 | 1/10 |
| | 10 | 200 | 0.40 | 1/20 |
| | 10 | 300 | 0.43 | 1/30 |
| | 10 | 400 | 0.47 | 1/40 |
| | 10 | 500 | 0.50 | 1/50 |
| | 10 | 600 | 0.53 | 1/60 |
| | 10 | 800 | 0.60 | 1/80 |
| | 10 | 1000 | 0.67 | 1/100 |
| | 10 | 2000 | 1.00 | 1/200 |
| | 15 | 20 | 0.51 | 1/1.3 |
| | 15 | 30 | 0.51 | 1/2 |
| | 15 | 40 | 0.51 | 1/3 |
| | 15 | 50 | 0.52 | 1/3 |
| | 15 | 60 | 0.52 | 1/4 |
| | 15 | 80 | 0.53 | 1/5 |
| | 15 | 100 | 0.53 | 1/7 |
| | 15 | 200 | 0.57 | 1/13 |
| | 15 | 300 | 0.60 | 1/20 |
| | 15 | 400 | 0.63 | 1/27 |
| | 15 | 500 | 0.67 | 1/33 |
| | 15 | 600 | 0.70 | 1/40 |
| | 15 | 800 | 0.77 | 1/53 |
| | 15 | 1000 | 0.83 | 1/67 |
| | 15 | 2000 | 1.17 | 1/133 |
| | 20 | 30 | 0.68 | 1/1.5 |
| | 20 | 40 | 0.68 | 1/2 |
| | 20 | 50 | 0.68 | 1/2.5 |
| | 20 | 60 | 0.69 | 1/3 |
| | 20 | 80 | 0.69 | 1/4 |
| | 20 | 100 | 0.70 | 1/5 |
| | 20 | 200 | 0.73 | 1/10 |
| | 20 | 300 | 0.77 | 1/15 |
| | 20 | 400 | 0.80 | 1/20 |
| | 20 | 500 | 0.83 | 1/25 |
| | 20 | 600 | 0.87 | 1/30 |
| | 20 | 800 | 0.93 | 1/40 |
| | 20 | 1000 | 1.00 | 1/50 |
| | 30 | 0 | 1.00 | — |
| P. aeruginosa 15442 - M9GY (72 hours) | 0 | 40 | 1.00 | — |
| | 10 | 30 | 0.85 | 1/3 |
| | 10 | 40 | 1.10 | 1/4 |
| | 20 | 30 | 0.95 | 1/1.5 |
| | 40 | 30 | 1.15 | 1/0.75 |
| | 80 | 8 | 1.00 | 1/0.1 |
| | 100 | 0 | 1.00 | — |

The synergistic ratios of BIT/Cocamidopropyl PG-dimonium chloride phosphate range from 1/1.3 to 1/800. The BIT/Cocamidopropyl PG-dimonium chloride phosphate combinations show enhanced control of mold.

TABLE 23

First Component (A) = BIT
Second Component (B) = propylparaben

| Microorganism | $Q_a$ | $Q_b$ | SI | A/B |
|---|---|---|---|---|
| A. niger 16404 - PDB (3 days) | 0 | 1000 | 1.00 | — |
| | 2.5 | 600 | 0.73 | 1/240 |
| | 2.5 | 800 | 0.93 | 1/320 |
| | 2.5 | 1000 | 1.13 | 1/400 |
| | 5 | 600 | 0.85 | 1/120 |
| | 5 | 800 | 1.05 | 1/160 |
| | 5 | 1000 | 1.25 | 1/200 |
| | 10 | 300 | 0.80 | 1/30 |
| | 10 | 400 | 0.90 | 1/40 |
| | 10 | 500 | 1.00 | 1/50 |
| | 10 | 600 | 1.10 | 1/60 |

TABLE 23-continued

First Component (A) = BIT
Second Component (B) = propylparaben

| Microorganism | $Q_a$ | $Q_b$ | SI | A/B |
|---|---|---|---|---|
| | 15 | 200 | 0.95 | 1/13 |
| | 20 | 0 | 1.00 | — |
| P. aeruginosa 15442 - M9GY (24 hours) | 0 | 10000 | 1.00 | — |
| | 20 | 10000 | 1.33 | 1/500 |
| | 40 | 5000 | 1.17 | 1/125 |
| | 60 | 2000 | 1.20 | 1/33 |
| | 80 | 0 | 1.33 | — |

The synergistic ratios of BIT/propylparaben range from 1/13 to 1/320. The BIT/propylparaben combinations show enhanced control of mold.

TABLE 24

First Component (A) = BIT
Second Component (B) = Cis-1-(3-chloroallyl)-3,5,7-triaza-1-azoniaadamantane chloride

| Microorganism | $Q_a$ | $Q_b$ | SI | A/B |
|---|---|---|---|---|
| A. niger 16404 - PDB (3 days) | 0 | 800 | 1.00 | — |
| | 2.5 | 600 | 0.83 | 1/240 |
| | 2.5 | 800 | 1.08 | 1/320 |
| | 5 | 600 | 0.92 | 1/120 |
| | 5 | 800 | 1.17 | 1/160 |
| | 10 | 600 | 1.08 | 1/60 |
| | 20 | 400 | 1.17 | 1/20 |
| | 30 | 0 | 1.00 | — |
| P. aeruginosa 15442 - M9GY (24 hours) | 0 | 400 | 1.00 | — |
| | 20 | 300 | 1.08 | 1/15 |
| | 40 | 200 | 1.17 | 1/5 |
| | 60 | 100 | 1.25 | 1/1.7 |
| | 60 | 0 | 1.00 | — |
| E. coli 8739 - M9GY (48 hours) | 0 | 400 | 1.00 | — |
| | 5 | 300 | 1.25 | 1/60 |
| | 7.5 | 30 | 0.83 | 1/4 |
| | 7.5 | 40 | 0.85 | 1/5 |
| | 7.5 | 50 | 0.88 | 1/7 |
| | 7.5 | 60 | 0.90 | 1/8 |
| | 7.5 | 80 | 0.95 | 1/10 |
| | 7.5 | 100 | 1.00 | 1/13 |
| | 10 | 0 | 1.00 | — |
| C. albicans 10231 - PDB (24 hours) | 0 | 800 | 1.00 | — |
| | 5 | 400 | 0.75 | 1/80 |
| | 5 | 500 | 0.88 | 1/100 |
| | 5 | 600 | 1.00 | 1/120 |
| | 15 | 100 | 0.88 | 1/7 |
| | 15 | 200 | 1.00 | 1/13 |
| | 20 | 0 | 1.00 | — |

The synergistic ratios of BIT/Cis-1-(3-chloroallyl)-3,5,7-triaza-1-azoniaadamantane chloride range from 1/4 to 1/240. The BIT/Cis-1-(3-chloroallyl)-3,5,7-triaza-1-azoniaadamantane chloride combinations show enhanced control of bacteria, yeast and mold.

TABLE 25

First Component (A) = BIT
Second Component (B) = sodium dehydroacetic acid

| Microorganism | $Q_a$ | $Q_b$ | SI | A/B |
|---|---|---|---|---|
| A. niger 16404 - PDB (1 week) | 0 | 200 | 1.00 | — |
| | 10 | 200 | 1.33 | 1/20 |
| | 15 | 80 | 0.90 | 1/5 |
| | 15 | 100 | 1.00 | 1/7 |
| | 20 | 8 | 0.71 | 1/0.4 |
| | 20 | 10 | 0.72 | 1/0.5 |
| | 20 | 20 | 0.77 | 1/1 |
| | 20 | 30 | 0.82 | 1/1.5 |
| | 20 | 40 | 0.87 | 1/2 |
| | 20 | 50 | 0.92 | 1/2.5 |

TABLE 25-continued

First Component (A) = BIT
Second Component (B) = sodium dehydroacetic acid

| Microorganism | $Q_a$ | $Q_b$ | SI | A/B |
|---|---|---|---|---|
|  | 20 | 60 | 0.97 | 1/3 |
|  | 20 | 80 | 1.07 | 1/4 |
|  | 30 | 0 | 1.00 | — |
| *P. aeruginosa* 15442 - M9GY | 0 | 10000 | 1.00 | — |
| (24 hours) | 20 | 10000 | 1.33 | 1/500 |
|  | 40 | 10000 | 1.67 | 1/250 |
|  | 60 | 10000 | 2.00 | 1/167 |
|  | 60 | 0 | 1.00 | — |
| *E. coli* 8739 - M9GY | 0 | 10000 | 1.00 | — |
| (24 hours) | 2.5 | 10000 | 1.33 | 1/4000 |
|  | 5 | 10000 | 1.67 | 1/2000 |
|  | 7.5 | 0 | 1.00 | — |
| *C. albicans* 10231 - PDB | 0 | 30 | 1.00 | — |
| (24 hours) | 5 | 20 | 0.83 | 1/4 |
|  | 5 | 30 | 1.17 | 1/6 |
|  | 10 | 20 | 1.00 | 1/2 |
|  | 20 | 20 | 1.33 | 1/1 |
|  | 30 | 0 | 1.00 | — |

The synergistic ratios of BIT/sodium dehydroacetic acid range from 1/0.4 to 1/5. The BIT/sodium dehydroacetic acid combinations show enhanced control of yeast and mold.

TABLE 26

First Component (A) = BIT
Second Component (B) = sodium benzoate

| Microorganism | $Q_a$ | $Q_b$ | SI | A/B |
|---|---|---|---|---|
| *A. niger* 16404 - PDB | 0 | 6000 | 1.00 | — |
| (1 week) | 2.5 | 5000 | 0.92 | 1/2000 |
|  | 2.5 | 6000 | 1.08 | 1/2400 |
|  | 5 | 4000 | 0.83 | 1/800 |
|  | 5 | 5000 | 1.00 | 1/1000 |
|  | 10 | 3000 | 0.83 | 1/300 |
|  | 20 | 1000 | 0.83 | 1/50 |
|  | 20 | 2000 | 1.00 | 1/100 |
|  | 30 | 0 | 1.00 | — |
| *P. aeruginosa* 15442 - M9GY | 0 | 10000 | 1.00 | — |
| (24 hours) | 20 | 10000 | 1.33 | 1/500 |
|  | 40 | 10000 | 1.67 | 1/250 |
|  | 60 | 10000 | 2.00 | 1/67 |
|  | 60 | 0 | 1.00 | — |
| *E. coli* 8739 - M9GY | 0 | 10000 | 1.00 | — |
| (24 hours) | 2.5 | 10000 | 1.33 | 1/4000 |
|  | 5 | 10000 | 1.67 | 1/2000 |
|  | 7.5 | 0 | 1.00 | — |
| *C. albicans* 10231 - PDB | 0 | 2000 | 1.00 | — |
| (48 hours) | 5 | 800 | 0.57 | 1/160 |
|  | 5 | 1000 | 0.67 | 1/200 |
|  | 5 | 2000 | 1.17 | 1/400 |
|  | 10 | 400 | 0.53 | 1/40 |
|  | 10 | 500 | 0.58 | 1/50 |
|  | 10 | 600 | 0.63 | 1/60 |
|  | 10 | 800 | 0.73 | 1/80 |
|  | 10 | 1000 | 0.83 | 1/100 |
|  | 10 | 2000 | 1.33 | 1/200 |
|  | 15 | 300 | 0.65 | 1/20 |
|  | 15 | 400 | 0.70 | 1/27 |
|  | 15 | 500 | 0.75 | 1/33 |
|  | 15 | 600 | 0.80 | 1/40 |
|  | 15 | 800 | 0.90 | 1/53 |
|  | 15 | 1000 | 1.00 | 1/67 |
|  | 20 | 100 | 0.72 | 1/5 |
|  | 20 | 200 | 0.77 | 1/10 |
|  | 20 | 300 | 0.82 | 1/15 |
|  | 20 | 400 | 0.87 | 1/20 |
|  | 20 | 500 | 0.92 | 1/25 |
|  | 20 | 600 | 0.97 | 1/30 |
|  | 20 | 800 | 1.07 | 1/40 |
|  | 30 | 0 | 1.00 | — |

The synergistic ratios of BIT/sodium benzoate range from 1/5 to 1/2000. The BIT/sodium benzoate combinations show enhanced control of yeast and mold.

TABLE 27

First Component (A) = BIT
Second Component (B) = Sodium hydroxymethylglycinate

| Microorganism | $Q_a$ | $Q_b$ | SI | A/B |
|---|---|---|---|---|
| *A. niger* 16404 - PDB | 0 | 600 | 1.00 | — |
| (3 days) | 5 | 500 | 1.08 | 1/100 |
|  | 10 | 500 | 1.33 | 1/50 |
|  | 15 | 300 | 1.25 | 1/20 |
|  | 20 | 0 | 1.00 | — |
| *P. aeruginosa* 15442 - M9GY | 0 | 2000 | 1.00 | — |
| (24 hours) | 10 | 1000 | 0.67 | 1/100 |
|  | 10 | 2000 | 1.17 | 1/200 |
|  | 20 | 1000 | 0.83 | 1/50 |
|  | 20 | 2000 | 1.33 | 1/100 |
|  | 30 | 800 | 0.90 | 1/27 |
|  | 40 | 600 | 0.97 | 1/15 |
|  | 60 | 500 | 1.25 | 1/8 |
|  | 60 | 0 | 1.00 | — |

The synergistic ratios of BIT/Sodium hydroxymethylglycinate range from 1/27 to 1/100. The BIT/Sodium hydroxymethylglycinate combinations show enhanced control of bacteria.

TABLE 28

First Component (A) = BIT
Second Component (B) = zinc pyrithione

| Microorganism | $Q_a$ | $Q_b$ | SI | A/B |
|---|---|---|---|---|
| *A. niger* 16404 - PDB | 0 | 8 | 1.00 | — |
| (1 week) | 2.5 | 5 | 0.71 | 1/2 |
|  | 2.5 | 6 | 0.83 | 1/2.4 |
|  | 2.5 | 8 | 1.08 | 1/3.2 |
|  | 5 | 8 | 1.17 | 1/2 |
|  | 10 | 8 | 1.33 | 1/0.8 |
|  | 20 | 3 | 1.04 | 1/0.15 |
|  | 30 | 0 | 1.00 | — |
| *P. aeruginosa* 15442 - M9GY | 0 | 80 | 1.00 | — |
| (48 hours) | 10 | 20 | 0.35 | 1/2 |
|  | 10 | 30 | 0.48 | 1/3 |
|  | 10 | 40 | 0.60 | 1/4 |
|  | 10 | 50 | 0.73 | 1/5 |
|  | 10 | 60 | 0.85 | 1/6 |
|  | 10 | 80 | 1.10 | 1/8 |
|  | 20 | 20 | 0.45 | 1/1 |
|  | 20 | 30 | 0.58 | 1/1.5 |
|  | 20 | 40 | 0.70 | 1/2 |
|  | 20 | 50 | 0.83 | 1/2.5 |
|  | 20 | 60 | 0.95 | 1/3 |
|  | 20 | 80 | 1.20 | 1/4 |
|  | 30 | 20 | 0.55 | 1/0.7 |
|  | 30 | 40 | 0.80 | 1/1 |
|  | 30 | 50 | 0.93 | 1/2 |
|  | 30 | 60 | 1.05 | 1/2 |
|  | 40 | 20 | 0.65 | 1/0.5 |
|  | 40 | 30 | 0.78 | 1/0.75 |
|  | 40 | 40 | 0.90 | 1/1 |
|  | 40 | 50 | 1.03 | 1/1.25 |
|  | 50 | 10 | 0.63 | 1/0.2 |
|  | 50 | 20 | 0.75 | 1/0.4 |

TABLE 28-continued

First Component (A) = BIT
Second Component (B) = zinc pyrithione

| Microorganism | $Q_a$ | $Q_b$ | SI | A/B |
|---|---|---|---|---|
| | 50 | 30 | 0.88 | 1/0.6 |
| | 50 | 40 | 1.00 | 1/0.8 |
| | 60 | 6 | 0.68 | 1/0.1 |
| | 60 | 8 | 0.70 | 1/0.13 |
| | 60 | 10 | 0.73 | 1/0.17 |
| | 60 | 20 | 0.85 | 1/0.3 |
| | 60 | 30 | 0.98 | 1/0.5 |
| | 60 | 40 | 1.10 | 1/0.7 |
| | 80 | 3 | 0.84 | 1/0.04 |
| | 80 | 4 | 0.85 | 1/0.05 |
| | 80 | 5 | 0.86 | 1/0.06 |
| | 80 | 6 | 0.88 | 1/0.075 |
| | 80 | 8 | 0.90 | 1/0.1 |
| | 80 | 10 | 0.93 | 1/0.125 |
| | 80 | 20 | 1.05 | 1/0.25 |
| | 100 | 0 | 1.00 | — |

The synergistic ratios of BIT/zinc pyrithione range from 1/0.04 to 1/6. The BIT/zinc pyrithione combinations show enhanced control of bacteria and mold.

The invention claimed is:

1. A microbicidal composition comprising:
   (a) 1,2-benzisothiazolin-3-one; and
   (b) at least one microbicide selected from the group consisting of benzalkonium chloride, benzethonium chloride, benzyl alcohol, caprylyl glycol, chlorphenesin, diazolidinyl urea, ethylparaben, imidazolidinyl urea, methylparaben, phenoxyethanol, linoleamidopropyl PG-dimonium chloride phosphate, cocamidopropyl PG-dimonium chloride phosphate, propylparaben, Cis-1-(3-chloroallyl)-3,5,7-triaza-1-azoniaadamantane chloride, dehydroacetic acid or its salts, benzoic acid or its salts, and sodium hydroxymethylglycinate
   wherein a weight ratio of 1,2-benzisothiazolin-3-one to benzalkonium chloride is from 1:0.025 to 1:40, a weight ratio of 1,2-benzisothiazolin-3-one to benzethonium chloride is from 1:0.13 to 1:3, a weight ratio of 1,2-benzisothiazolin-3-one to benzyl alcohol is from 1:0.4 to 1:35, a weight ratio of 1,2-benzisothiazolin-3-one to caprylyl glycol is from 1:0.7 to 1:67, a weight ratio of 1,2-benzisothiazolin-3-one to chlorphenesin is from 1:20 to 1:50, a weight ratio of 1,2-benzisothiazolin-3-one to diazolidinyl urea is from 1:1 to 1:100, a weight ratio of 1,2-benzisothiazolin-3-one to ethylparaben is from 1:13 to 1:400, a weight ratio of 1,2-benzisothiazolin-3-one to imidazolidinyl urea is from 1:20 to 1:30, a weight ratio of 1,2-benzisothiazolin-3-one to methylparaben is from 1:3 to 1:240, a weight ratio of 1,2-benzisothiazolin-3-one to phenoxyethanol is from 1:2.5 to 1:800, a weight ratio of 1,2-benzisothiazolin-3-one to linoleamidopropyl PG-dimonium chloride phosphate is from 1:0.5 to 1:800, a weight ratio of 1,2-benzisothiazolin-3-one to cocamidopropyl PG-dimonium chloride phosphate is from 1:1.3 to 1:800, a weight ratio of 1,2-benzisothiazolin-3-one to propylparaben is from 1:13 to 1:320, a weight ratio of 1,2-benzisothiazolin-3-one to Cis-1-(3-chloroallyl)-3,5,7-triaza-1-azoniaadamantane chloride is from 1:4 to 1:240, a weight ratio of 1,2-benzisothiazolin-3-one to dehydroacetic acid or its salts is from 1:0.4 to 1:5, a weight ratio of 1,2-benzisothiazolin-3-one to benzoic acid or its salts is from 1:5 to 1:2000, and a weight ratio of 1,2-benzisothiazolin-3-one to sodium hydroxymethylglycinate is from 1:27 to 1:100.

2. A microbicidal composition comprising:
   (a) 2-methyl-4-isothiazolin-3-one; and
   (b) at least one microbicide selected from the group consisting of caprylyl glycol, chlorphenesin, hexamidine diisethionate, hexetidine, linoleamidopropyl PG-dimonium chloride phosphate, cocamidopropyl PG-dimonium chloride phosphate and dehydroacetic acid or its salts
   wherein a weight ratio of 2-methyl-4-isothiazolin-3-one to caprylyl glycol is from 1:0.5 to 1:20, a weight ratio of 2-methyl-4-isothiazolin-3-one to chlorphenesin is from 1:1.2 to 1:600, a weight ratio of 2-methyl-4-isothiazolin-3-one to hexamidine diisethionate is from 1:0.001 to 1:60, a weight ratio of 2-methyl-4-isothiazolin-3-one to hexetidine is from 1:0.002, to 1:250, a weight ratio of 2-methyl-4-isothiazolin-3-one to linoleamidopropyl PG-dimonium chloride phosphate is from 1:0.3 to 1:600, a weight ratio of 2-methyl-4-isothiazolin-3-one to cocamidopropyl PG-dimonium chloride phosphate is from 1:0.03 to 1:80, a weight ratio of 2-methyl-4-isothiazolin-3-one to dehydroacetic acid or its salts is from 1:0.25 to 1:3.

* * * * *

(12) EX PARTE REEXAMINATION CERTIFICATE (7108th)
United States Patent
Levy et al.

(10) Number: US 7,468,384 C1
(45) Certificate Issued: Oct. 13, 2009

(54) MICROBICIDAL COMPOSITION

(75) Inventors: Richard Levy, Valbonne (FR); Megan Anne Diehl, Line Lexington, PA (US); Dolores Ann Shaw, Collegeville, PA (US); Eileen Fleck Warwick, Lansdale, PA (US)

(73) Assignee: Rohm and Haas Company, Philadelphia, PA (US)

Reexamination Request:
No. 90/009,452, Apr. 13, 2009

Reexamination Certificate for:
Patent No.: 7,468,384
Issued: Dec. 23, 2008
Appl. No.: 11/265,654
Filed: Nov. 2, 2005

Related U.S. Application Data
(60) Provisional application No. 60/628,326, filed on Nov. 16, 2004.

(51) Int. Cl.
*A01N 43/80* (2006.01)
*A61K 31/425* (2006.01)

(52) U.S. Cl. .................................................. 514/373
(58) Field of Classification Search .................. None
See application file for complete search history.

(56) References Cited

U.S. PATENT DOCUMENTS 5,008,150 A    4/1991  Ashida et al.
2005/0228032 A1  10/2005  Merianos et al.

FOREIGN PATENT DOCUMENTS

EP    1184507    3/2002
JP    1999/071211 A    3/1999

*Primary Examiner*—Dwayne C Jones

(57) ABSTRACT

A microbicidal composition of 1,2-benzisothiazolin-3-one; and at least one of benzalkonium chloride, benzethonium chloride, benzyl alcohol, caprylyl glycol, chlorphenesin, diazolidinyl urea, ethylparaben, imidazolidinyl urea, methylparaben, phenoxyethanol, linoleamidopropyl PG-dimonium chloride phosphate, cocamidopropyl PG-dimonium chloride phosphate, propylparaben, cis-1-(3-chloroallyl)-3,5,7-triaza-1-azoniaadamantane chloride, dehydroacetic acid or its salts, benzoic acid or its salts, and sodium hydroxymethylglycinate.

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

New claims 3–10 are added and determined to be patentable.

Claim 2 was not reexamined.

1. A microbicidal composition comprising:
   (a) 1,2-benzisothiazolin-3-one; and
   (b) at least one microbicide selected from the group consisting of [benzalkonium chloride, benzethonium chloride,] benzyl alcohol, caprylyl glycol, chlorphenesin, diazolidinyl urea, ethylparaben, imidazolidinyl urea, [methylparaben,] phenoxyethanol, linoleamidopropyl PG-dimonium chloride phosphate, cocamidopropyl PG-dimonium chloride phosphate, propylparaben, Cis-1-(3-chloroallyl)-3,5,7-triaza-1-azoniaadamantane chloride, dehydroacetic acid or its salts, benzoic acid or its salts, and sodium hydroxymethylglycinate
   wherein [a weight ratio of 1,2-benzisothiazolin-3-one to benzalkonium chloride is from 1:0.025 to 1:40, a weight ratio of 1,2-benzisothiazolin-3-one to benzethonium chloride is from 1:0.13 to 1:3,] a weight ratio of 1,2-benzisothiazolin-3-one to benzyl alcohol is from [1:0.4] *1:10* to 1:35, a weight ratio of 1,2-benzisothiazolin-3-one to caprylyl glycol is from [1:0.7] *1:33* to 1:67, a weight ratio of 1,2-benzisothiazolin-3-one to chlorphenesin is from 1:20 to 1:50, a weight ratio of 1,2-benzisothiazolin-3-one to diazolidinyl urea is from 1:1 to 1:100, a weight ratio of 1,2-benzisothiazolin-3-one to ethylparaben is from 1:13 to 1:400, a weight ratio of 1,2-benzisothiazolin-3-one to imidazolidinyl urea is from 1:20 to 1:30, [a weight ratio of 1,2-benzisothiazolin-3-one to methylparaben is from 1:3 to 1:240,] a weight ratio of 1,2-benzisothiazolin-3-one to phenoxyethanol is from [1:2.5] *1:100* to 1:800, a weight ratio of 1,2-benzisothiazolin-3-one to linoleamidopropyl PG-dimonium chloride phosphate is from 1:0.5 to 1:800, a weight ratio of 1,2-benzisothiazolin-3-one to cocamidopropyl PG-dimonium chloride phosphate is from 1:1.3 to 1:800, a weight ratio of 1,2-benzisothiazolin-3-one to propylparaben is from 1:13 to 1:320, a weight ratio of 1,2-benzisothiazolin-3-one to Cis-1-(3-chloroallyl)-3,5,7-triaza-1-azoniaadamantane chloride is from 1:4 to 1:240, a weight ratio of 1,2-benzisothiazolin-3-one to dehydroacetic acid or its salts is from 1:0.4 to 1:5, a weight ratio of 1,2-benzisothiazolin-3-one to benzoic acid or its salts is from 1:5 to 1:2000, and a weight ratio of 1,2-benzisothiazolin-3-one to sodium hydroxymethylglycinate is from 1:27 to 1:100.

*3. The microbicidal composition of claim 1 in which said at least one microbicide is benzyl alcohol and a weight ratio of 1,2-benzisothiazolin-3-one to benzyl alcohol is from 1:10 to 1:35.*

*4. The microbicidal composition of claim 1 in which said at least one microbicide is caprylyl glycol and a weight ratio of 1,2-benzisothiazolin-3-one to caprylyl glycol is from 1:33 to 1:67.*

*5. The microbicidal composition of claim 4 in which the weight ratio of 1,2-benzisothiazolin-3-one to caprylyl glycol is from 1:53 to 1:67.*

*6. The microbicidal composition of claim 1 in which said at least one microbicide is dehydroacetic acid and a weight ratio of 1,2-benzisothiazolin-3-one to dehydroacetic acid is from 1:0.4 to 1:5.*

*7. The microbicidal composition of claim 1 in which said at least one microbicide is benzoic acid and a weight ratio of 1,2-benzisothiazolin-3-one to benzoic acid is from 1:5 to 1:2000.*

*8. The microbicidal composition of claim 1 in which said at least one microbicide is phenoxyethanol and a weight ratio of 1,2-benzisothiazolin-3-one to phenoxyethanol is from 1:100 to 1:800.*

*9. The microbicidal composition of claim 1 in which said at least one microbicide is ethylparaben and a weight ratio of 1,2-benzisothiazolin-3-one to ethylparaben is from 1:13 to 1:400.*

*10. The microbicidal composition of claim 1 in which said at least one microbicide is propylparaben and a weight ratio of 1,2-benzisothiazolin-3-one to propylparaben is from 1:13 to 1:320.*

\* \* \* \* \*